United States Patent
Talbert et al.

(10) Patent No.: US 8,648,932 B2
(45) Date of Patent: Feb. 11, 2014

(54) SYSTEM, APPARATUS AND METHODS FOR PROVIDING A SINGLE USE IMAGING DEVICE FOR STERILE ENVIRONMENTS

(75) Inventors: Joshua D. Talbert, Cottonwood Heights, UT (US); Jeremiah D. Henley, Midvale, UT (US); Donald M. Wichern, South Ogden, UT (US)

(73) Assignee: Olive Medical Corporation, Salt Lake City, UT (US)

( * ) Notice: Subject to any disclaimer, the term of this patent is extended or adjusted under 35 U.S.C. 154(b) by 1176 days.

(21) Appl. No.: 12/541,067

(22) Filed: Aug. 13, 2009

(65) Prior Publication Data

US 2011/0037876 A1 Feb. 17, 2011

(51) Int. Cl.
*H04N 5/76* (2006.01)
*H04N 5/225* (2006.01)
*H04N 5/228* (2006.01)

(52) U.S. Cl.
USPC ............... 348/231.99; 348/340; 348/222.1

(58) Field of Classification Search
None
See application file for complete search history.

(56) References Cited

U.S. PATENT DOCUMENTS

| | | |
|---|---|---|
| 3,796,220 A | 3/1974 | Bredemeier |
| 3,858,577 A | 1/1975 | Bass et al. |
| 4,011,403 A | 3/1977 | Epstein et al. |
| 4,153,356 A | 5/1979 | Hama |
| 4,350,150 A | 9/1982 | Kubota et al. |
| 4,429,686 A | 2/1984 | Hosoda |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkle et al. |
| 4,800,424 A | 1/1989 | Noguchi |
| 4,831,444 A | 5/1989 | Kato |
| 4,888,639 A | 12/1989 | Yabe et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,042,915 A | 8/1991 | Akutsu et al. |
| 5,115,309 A | 5/1992 | Hang |
| 5,168,863 A | 12/1992 | Kurtzer |
| 5,227,662 A | 7/1993 | Ohno et al. |
| 5,237,403 A | 8/1993 | Sugimoto et al. |
| 5,277,172 A | 1/1994 | Sugimoto |

(Continued)

FOREIGN PATENT DOCUMENTS

| | | |
|---|---|---|
| WO | 94/13191 | 6/1994 |
| WO | 2004/093438 | 10/2004 |
| WO | 2009/135255 | 11/2009 |

*Primary Examiner* — Andy Rao
*Assistant Examiner* — Tyler Edwards
(74) *Attorney, Agent, or Firm* — Terrence J. Edwards

(57) ABSTRACT

A system, apparatus and methods for providing a single use imaging device for sterile environments is disclosed and described. A single use high definition camera used for general purpose surgical procedures including, but not limited to: arthroscopic, laparoscopic, gynecologic, and urologic procedures, may comprise an imaging device that is a sterile and designed to ensure single use. The imaging device may have a single imaging sensor, either CCD (charge coupled device) or CMOS (complementary metal oxide semiconductor), encased in a housing. The imaging device may further include the ability to be attached to an optical coupling device, using C-Mount threads or another proprietary or unique connection method. The imaging device may further include a cable to transmit data to and from a camera control unit.

76 Claims, 20 Drawing Sheets

(56) References Cited

U.S. PATENT DOCUMENTS

| | | |
|---|---|---|
| 5,289,555 A | 2/1994 | Sanso |
| 5,307,804 A | 5/1994 | Bonnett |
| 5,381,784 A | 1/1995 | Adair |
| 5,400,267 A | 3/1995 | Denen et al. |
| 5,489,801 A | 2/1996 | Blish, II |
| 5,494,483 A | 2/1996 | Adair |
| 5,522,006 A | 5/1996 | Takeuchi et al. |
| 5,576,781 A | 11/1996 | Deleeuw |
| 5,594,282 A | 1/1997 | Otsuki |
| 5,614,763 A | 3/1997 | Womack |
| 5,757,075 A | 5/1998 | Kitaoka |
| 5,879,289 A | 3/1999 | Yarush et al. |
| 5,896,166 A | 4/1999 | D'Alfonso et al. |
| 5,929,901 A | 7/1999 | Adair et al. |
| 5,986,693 A | 11/1999 | Adair et al. |
| 6,043,839 A | 3/2000 | Adair et al. |
| 6,059,776 A | 5/2000 | Gatto |
| 6,059,793 A | 5/2000 | Pagedas |
| 6,211,904 B1 | 4/2001 | Adair et al. |
| 6,275,255 B1 | 8/2001 | Adair et al. |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,390,972 B1 | 5/2002 | Speier et al. |
| 6,404,048 B2 | 6/2002 | Akram |
| 6,424,369 B1 | 7/2002 | Adair et al. |
| 6,436,032 B1 | 8/2002 | Eto et al. |
| 6,452,626 B1 | 9/2002 | Adair et al. |
| 6,588,884 B1 | 7/2003 | Furlani et al. |
| 6,720,810 B1 | 4/2004 | New |
| 6,726,620 B2 | 4/2004 | Shibata et al. |
| 6,784,940 B1 | 8/2004 | Takazawa et al. |
| 6,812,949 B1 | 11/2004 | Switzer et al. |
| 6,847,490 B1 * | 1/2005 | Nordstrom et al. ............ 359/642 |
| 6,862,036 B2 | 3/2005 | Adair et al. |
| 6,976,954 B2 | 12/2005 | Takahashi |
| 6,982,740 B2 | 1/2006 | Adair et al. |
| 6,982,742 B2 | 1/2006 | Adair et al. |
| 6,997,871 B2 | 2/2006 | Sonnenschein et al. |
| 7,002,621 B2 | 2/2006 | Adair et al. |
| 7,018,331 B2 | 3/2006 | Chang et al. |
| 7,030,904 B2 | 4/2006 | Adair et al. |
| 7,061,117 B2 | 6/2006 | Yang et al. |
| 7,070,560 B2 | 7/2006 | Takahashi |
| 7,088,398 B1 | 8/2006 | Wolf et al. |
| 7,115,091 B2 | 10/2006 | Root et al. |
| 7,193,519 B2 | 3/2007 | Root et al. |
| 7,227,469 B2 | 6/2007 | Varner et al. |
| 7,230,615 B2 | 6/2007 | Wang et al. |
| 7,258,546 B2 | 8/2007 | Beier et al. |
| 7,274,390 B2 | 9/2007 | Sevat et al. |
| 7,276,785 B2 | 10/2007 | Bauer et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 12/2007 | Couvillon, Jr. |
| 7,317,955 B2 | 1/2008 | McGreevy |
| 7,331,523 B2 | 2/2008 | Meier et al. |
| 7,339,982 B2 | 3/2008 | Wood, Jr. |
| 7,386,084 B2 | 6/2008 | Yin |
| 7,402,811 B2 | 7/2008 | Hatanaka et al. |
| 7,443,296 B2 | 10/2008 | Mezhinsky et al. |
| 7,517,351 B2 | 4/2009 | Culp et al. |
| 7,535,037 B2 | 5/2009 | Lyu |
| 7,542,069 B2 | 6/2009 | Tashiro |
| 7,551,059 B2 | 6/2009 | Farrier |
| 7,568,619 B2 | 8/2009 | Todd et al. |
| 7,578,786 B2 | 8/2009 | Boulais et al. |
| 7,598,686 B2 | 10/2009 | Lys et al. |
| 7,599,439 B2 | 10/2009 | Lavelle et al. |
| 7,768,562 B2 | 8/2010 | Boemler |
| 7,795,650 B2 | 9/2010 | Eminoglu et al. |
| 7,800,192 B2 | 9/2010 | Venezia et al. |
| 7,824,328 B2 * | 11/2010 | Gattani et al. ............ 600/117 |
| 7,868,283 B2 | 1/2011 | Mabuchi |
| 7,871,373 B2 | 1/2011 | Yamada |
| 7,880,662 B2 | 2/2011 | Bogaerts |
| 2001/0041825 A1 | 11/2001 | Shibata et al. |
| 2001/0052930 A1 | 12/2001 | Adair et al. |
| 2002/0017611 A1 | 2/2002 | Tashiro et al. |
| 2002/0067408 A1 | 6/2002 | Adair et al. |
| 2002/0080248 A1 | 6/2002 | Adair et al. |
| 2002/0163578 A1 | 11/2002 | Adair et al. |
| 2002/0180867 A1 | 12/2002 | Adair et al. |
| 2003/0187586 A1 | 10/2003 | Katzenmaier et al. |
| 2004/0049215 A1 | 3/2004 | Snow et al. |
| 2004/0078494 A1 | 4/2004 | Lennox et al. |
| 2004/0111012 A1 | 6/2004 | Whitman |
| 2004/0169771 A1 | 9/2004 | Washington et al. |
| 2004/0249267 A1 | 12/2004 | Gilboa |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |
| 2006/0022234 A1 | 2/2006 | Adair et al. |
| 2006/0221230 A1 | 10/2006 | Dutta et al. |
| 2006/0249765 A1 | 11/2006 | Hsieh |
| 2006/0293563 A1 | 12/2006 | Banik et al. |
| 2006/0293565 A1 | 12/2006 | Uchimura et al. |
| 2007/0030345 A1 | 2/2007 | Amling et al. |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0297970 A1 | 12/2007 | Ng |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0258042 A1 | 10/2008 | Krymski |
| 2008/0287798 A1 | 11/2008 | Lee et al. |
| 2008/0309810 A1 | 12/2008 | Smith et al. |
| 2008/0312505 A1 * | 12/2008 | Schaaf ............ 600/139 |
| 2008/0316319 A1 | 12/2008 | Nomoto |
| 2009/0015301 A1 | 1/2009 | Marchesini et al. |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0076329 A1 | 3/2009 | Su et al. |
| 2009/0082630 A1 | 3/2009 | Tulley |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0173974 A1 | 7/2009 | Shah et al. |
| 2009/0184349 A1 | 7/2009 | Dungan |
| 2009/0192390 A1 | 7/2009 | Berguer et al. |
| 2009/0200624 A1 | 8/2009 | Dai et al. |
| 2009/0203966 A1 | 8/2009 | Mizuyoshi |
| 2009/0212397 A1 | 8/2009 | Tuttle |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0306478 A1 | 12/2009 | Mizuyoshi |
| 2009/0322911 A1 | 12/2009 | Blanquart |

(56) References Cited

U.S. PATENT DOCUMENTS

| | | |
|---|---|---|
| 2009/0322912 A1 | 12/2009 | Blanquart |
| 2010/0026824 A1 | 2/2010 | Chen |
| 2010/0059802 A1 | 3/2010 | Chen |
| 2010/0118932 A1 | 5/2010 | Luo et al. |
| 2010/0178722 A1 | 7/2010 | de Graff et al. |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2011/0028790 A1 | 2/2011 | Farr et al. |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049491 A1 | 3/2011 | Nakatani et al. |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0208004 A1 | 8/2011 | Feingold et al. |
| 2011/0238977 A1 | 9/2011 | Talbert et al. |

\* cited by examiner

SYSTEM, APPARATUS AND METHODS FOR PROVIDING A SINGLE USE IMAGING DEVICE FOR STERILE ENVIRONMENTS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

The disclosure relates generally to imaging devices used during surgical procedures to visualize a surgical area, and more particularly, but not necessarily entirely, to an imaging device for use with and communicating with a control unit and a system, method and process of communicating between an imaging device and a control unit.

Endoscopic surgery is experiencing rapid growth in the medical field. Endoscopy is a minimally invasive surgical procedure that is used to analyze the interior of a body cavity or interior surfaces of an organ by inserting a tubular member into the body cavity through a minor or minimal incision. A conventional endoscope is generally an instrument with a light source and an image sensor or device for visualizing the interior a body cavity. A wide range of applications have been developed for the general field of endoscopes including, but not necessarily limited to: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngoneproscope, sigmoidoscope, thoracoscope, and utererscope (hereinafter referred to generally as "endoscope"). The advantages of endoscopy include smaller surgical incisions and less soft tissue damage. As a result, there is significantly less discomfort and pain for the patient as well as a decrease in recovery time.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope.

As part of forming an image of the surgical site, the endoscope includes a light source and an image sensor. Endoscopes may also incorporate more than one tubular member for observation or operation within the body, such as a working channel for passing diagnostic, monitoring, treatment, or surgical tools through the endoscope. Endoscopes include glass lenses and an adjustable ocular or eye piece, a lateral connection for a light conductor, an adaptor that allows focusing, and a camera head. This configuration is also called a video endoscope.

It is axiomatic that strict sterilization of the operating room and surgical equipment is required during any surgery. The strict hygiene and sterilization conditions required in a "surgical theater," i.e., operating or treatment room, necessitate the highest possible sterility of all medical devices and equipment. Part of that sterilization process is the need to sterilize anything that comes in contact with the patient, including the endoscope and its attachments and components. In recent years there has been a trend of providing a single use endoscope and components as a packaged, sterilized product, similar to a package containing a surgical implant, such as a knee or hip implant. In terms of endoscopy, instead of using endoscopes that have been reconditioned for each new surgery through traditional sterilization procedures, it means using a single use endoscope and components that are delivered to the hospital in a sterilized package. Due to this trend, it has become increasingly difficult to ensure that each endoscope and its components are properly cared for, used and sterilized for single use and not simply re-sterilized using traditional sterilization procedures.

Traditional drawbacks or problems of video endoscopes include a lack of image quality, the need for sterilization and high manufacturing cost. To address these and potentially other problems, the disclosure utilizes unique imaging devices or sensors in addition to a unique method, system and process for providing and reclaiming single use imaging devices.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein.

SUMMARY OF THE DISCLOSURE

An embodiment may comprise a single use camera used for general purpose surgical procedures including, but not limited to: arthroscopic, laparoscopic, gynecologic, and urologic. An embodiment may comprise an imaging device that is a sterile and designed to ensure single use. An embodiment may be an imaging device that comprises a single imaging sensor, either CCD (charge coupled device) or CMOS (complementary metal oxide semiconductor), encased in a molded plastic housing. The imaging device may further comprise the means to be attached to an optical coupling device, using C-Mount and CS-Mount threads or another proprietary or unique connection method. It is within the disclosure to include integrated optical systems, such that no specific coupling means is required. The imaging device may further comprise a cable or wireless method to transmit data to and from a camera control unit.

In an embodiment, information will be recorded in the memory of the imaging device each time it is used in a procedure or quality control (QC) checked at the manufacturer. This information may be used to evaluate usage time, expiration date, etc. An embodiment may comprise features to ensure that the imaging device is only used once and that the imaging device is safe for use. In an embodiment the imaging device may be fully covered in plastic with a neutral sensor heat sink exposed to ensure the camera head meets cardiac floating (CF) and body floating (BF) ISO standards. An embodiment may comprise an imaging device that may be stamped with the current time when plugged into a console in the field after a quality control check has been performed. This time may be used as a baseline for usage. If the imaging device is powered off for a predetermined period of time, which may be equivalent to a sterilization cycle, then the imaging device will not function. The imaging device may display an onscreen message telling the user that the camera has already been used and will not allow current operation. These features ensure the imaging device will not be used more than one time per sterilization cycle and further ensures that proper sterilization is performed by the manufacturer or other authorized source. This function is to protect the patient and the doctor from an invalid or unsafe use.

In an embodiment of an active imaging device may be attached to a control unit. The control unit will check the last sterilization date and ensure that the imaging device is no older than a predetermined safety date. If the imaging device is older than the required date, an onscreen warning will tell the user that the imaging device has expired and is unsafe for use. These features will protect the patient and the doctor from using a non-sterile imaging device.

In an embodiment a security code or some other means of identifying, and validating for use, an imaging device by a control unit maybe provided in order to verify that the imaging device is authorized for use. A validating security code or procedure of validation may be distributed to control units from a central database over the internet, by direct transfer from portable storage device such as USB device containing memory, another computer, or other storage device.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
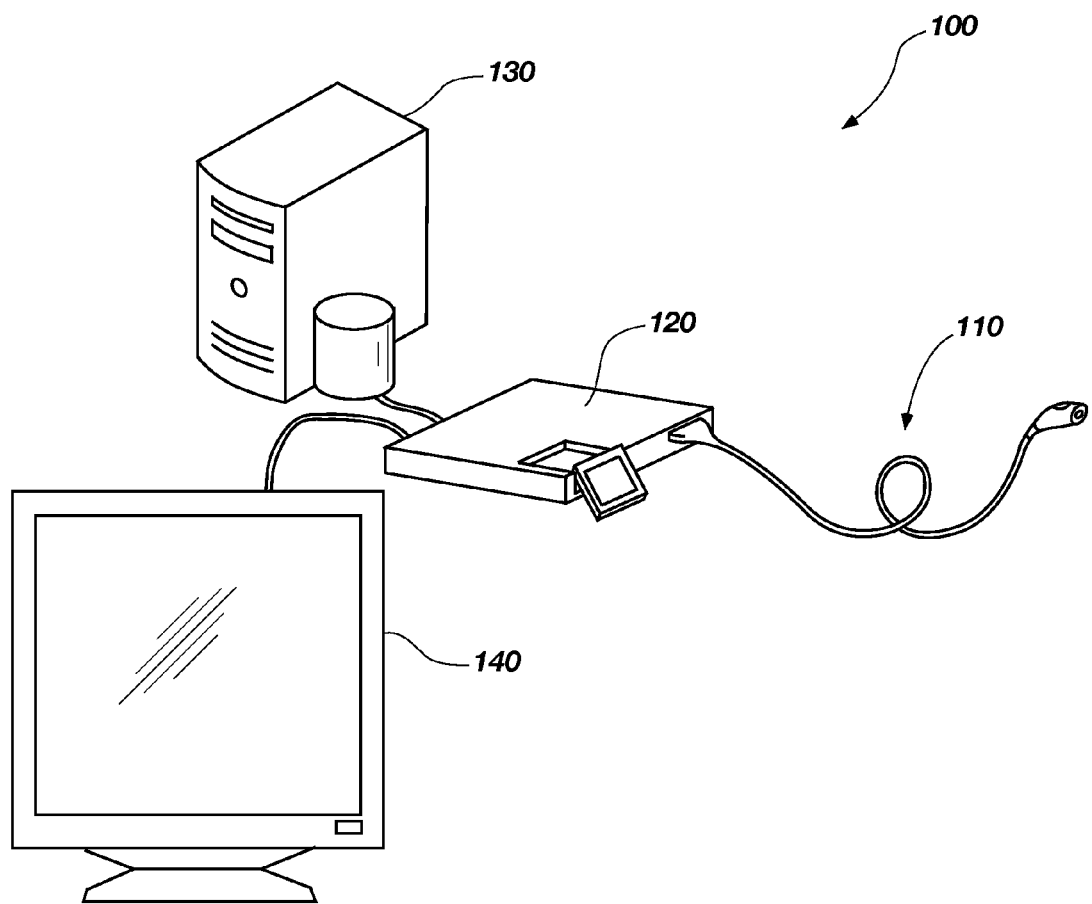
FIG. 1 is an illustration of an embodiment of the features of the disclosure and made in accordance with the teachings and principles of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for providing and reclaiming single use imaging devices are disclosed and described, it is to be understood that this disclosure is not limited to the particular embodiments, configurations, or process steps disclosed herein as such embodiments, configurations, or process steps may vary somewhat. It is also to be understood that the terminology employed herein is used for the purpose of describing particular embodiments only and is not intended to be limiting since the scope of the disclosure will be limited only by the appended claims, if any, and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

With reference primarily to FIG. 1, an embodiment of the features of the disclosure will be discussed generally. FIG. 1 illustrates a system 100 for providing a digital image using a remote imaging device 110 that may be tethered electronically and physically to a control unit 120. The control unit 120 may be configured to exchange data with imaging device 110 in order to provide single use functionality and safety in a sterile environment, such as an operating room, a doctor's office or dental office. Additionally, the control unit 120 may be electrically connected to a computer 130 or external monitor 140 for increased functionality.

Figure 2:
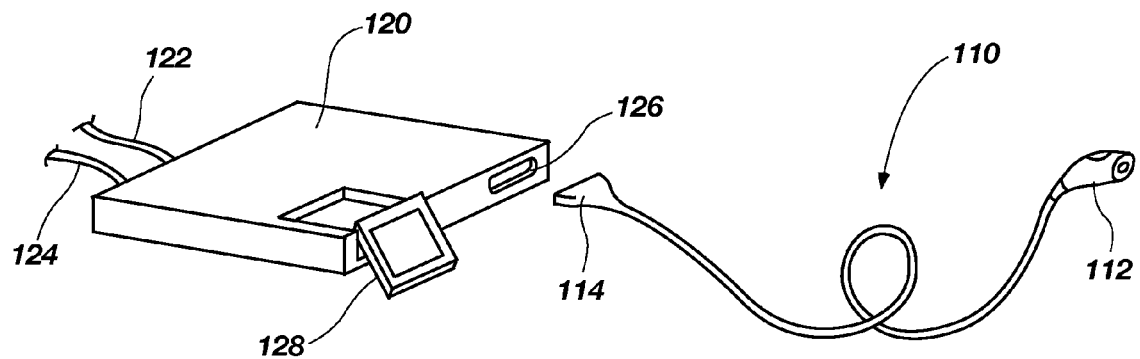
FIG. 2 is an illustration of an embodiment of an imaging system made in accordance with the teachings and principles of the disclosure.

Referring now to FIG. 2 where the imaging system 100 will be discussed in greater detail. As is illustrated in FIG. 2, the imaging device 110 can be connected or disconnected from the control unit 120 by way of an electronic connector 114 on the imaging device 110 that is configured to electronically and physically interact with a corresponding electronic connector 126 on the control unit 120. The ability to disconnect the imaging device 110 from the control unit 120 provides the ability to easily replace a used imaging device 110 for a sterilized, renewed imaging device 110. The imaging device 110 may have a head portion 112 generally positioned remotely from the electronic connector 114, thereby allowing greater mobility of the head portion 112 during use.

Also illustrated in FIG. 2 is an embodiment of the control unit 120 having an electronic connector 126 therein for receiving the corresponding electronic connector 114 of the imaging device 110. The control unit 120 may also have a display 128 for conveying information during a procedure to an operator or user. The display 128 may also comprise interactive functionality allowing an operator to enter commands or change what information is being displayed. Such functionality may be provided by a touch screen system as is commonly known. The control unit may also have video inputs 122 and video outputs 124 for transferring image data to other apparatuses for increased functionality. As illustrated in FIG. 1, common apparatuses may be a computer 130 or an external monitor 140.

Figure 3:
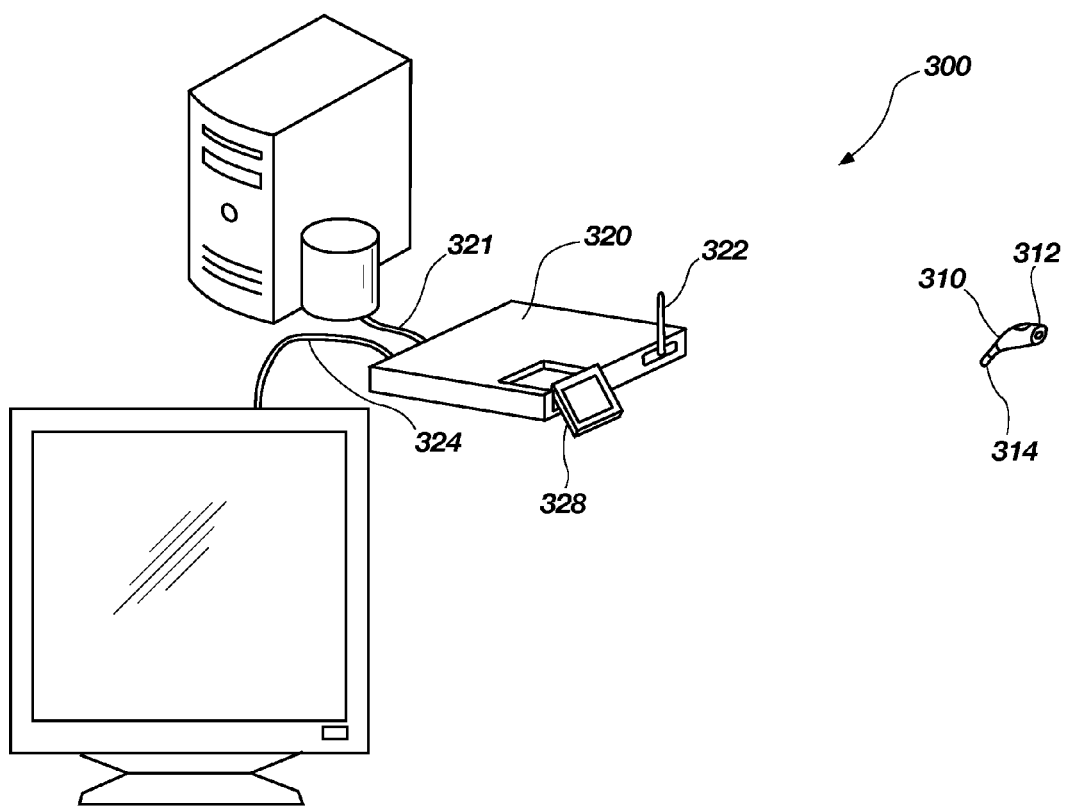
FIG. 3 is an illustration of an imaging system having wireless features made in accordance with the teachings and principles of the disclosure.

Referring now to FIG. 3 an imaging system 300 will be discussed having wireless capability and features. As is illustrated in FIG. 3, the imaging device 310 may communicate with a control unit 320 by way of wireless transmissions such as Wifi, infrared, bluetooth etc. Other forms of wireless non-tethered connectivity may also be used for providing communication between the imaging device 310 and control unit 320, including but not limited to, radio frequency from any available spectrum, infrared of all configurations, ultrasonic, and optical. The imaging device 310 may comprise a head portion 312 that houses an imaging sensor, memory and associated circuitry, which will be discussed in greater detail below. The head portion 312 may further comprise a wireless transceiver 314 for communicating with a corresponding wireless transceiver 322 housed in the control unit 320. The ability to separate the head portion 312 from the control unit 320 via wireless transmissions may provide for the easy replacement of used imaging devices for sterilized and renewed imaging devices. In other words, the wireless communication may be enabled by an electronic communication circuit that is a wireless communication transceiver configured to communicate wirelessly with a corresponding transceiver on said control unit using any of the above noted wireless technologies. The wireless functionality also allows for greater mobility of the head portion 312 during use. It will be appreciated that the wireless features and functionality may be incorporated into any of the embodiments disclosed herein or embodiments that fall within the scope of this disclosure.

Also illustrated in FIG. 3 is an embodiment of the control unit 320 having wireless capabilities and features. A transceiver 322 may be provided in or as part of the control unit 320 for receiving and transmitting wireless data to the imaging device 310. The control unit 320 may also have a display 328 for conveying information during a procedure to an operator or user. The display 328 may also comprise interactive functionality allowing an operator to enter commands or change what information is being displayed. Such functionality may be provided by a touch screen system as is commonly known. The control unit 320 may also have video inputs 321 and video outputs 324 for transferring image data to other apparatuses for increased functionality. As illustrated in FIG. 1, common apparatuses may be a computer 130 or an external monitor 140. It is within the scope of this disclosure to include an imaging system comprising both wired and wireless communication capabilities.

Figure 4:
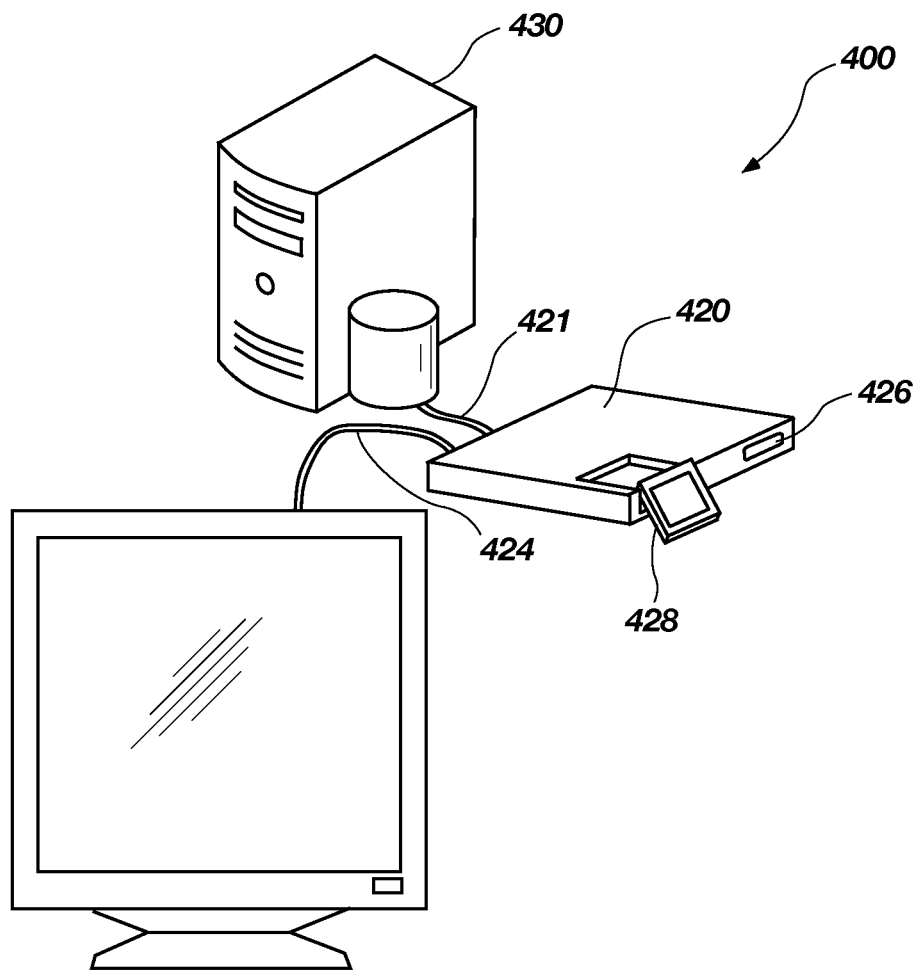
FIG. 4 is an illustration of an embodiment of a control unit disconnected from an imaging device, but illustrated as remaining connected to complementary apparatuses, and made in accordance with the teachings and principles of the disclosure.

Illustrated in FIG. 4 is an embodiment of the control unit 420 disconnected from an imaging device that is illustrated as being connected to complementary apparatuses. A connector 426 may be provided therein for transferring data to and from an imaging device. The ability to separate the imaging device may provide for the easy replacement of used imaging devices with sterilized and renewed imaging devices. The control unit 420 may also have a display 428 for conveying to an operator information during a procedure. The display 428 may also comprise interactive functionality allowing an operator to enter commands or change what information is being displayed. Such functionality may be provided by a touch screen system as is commonly known. The control unit may also have video inputs 421 and video outputs 424 for transferring image data to other apparatuses for increased functionality. Common apparatuses may be a computer 430 or an external monitor 440 there by increasing the technical functionality of the system 400. A computer 430 may be used for storing the digital output from the imaging system or may be used to enhance and provide further adjustment within the system. An external monitor 440 may be used to show real time digital images to aid an operator in the use of the system, or later review and study the recorded digital imagery.

Figure 5:
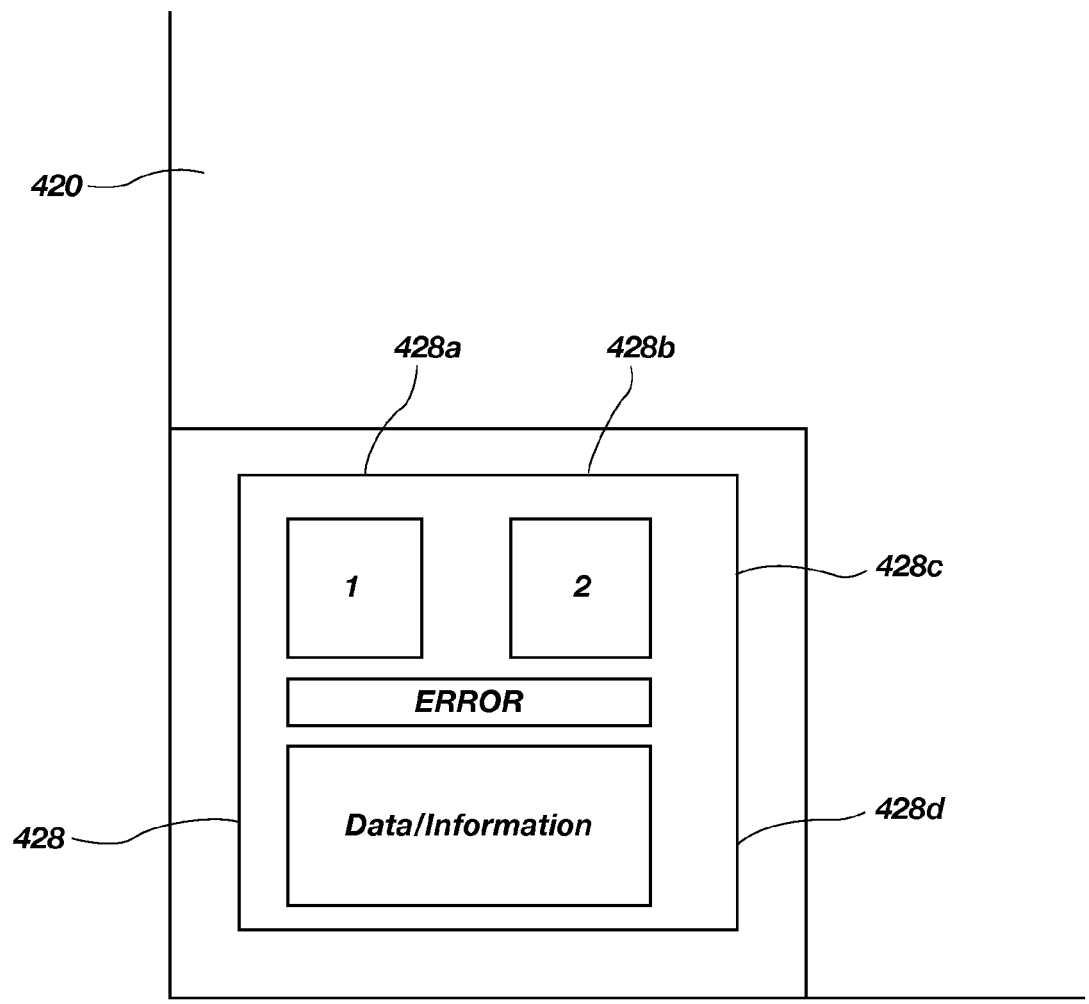
FIG. 5 is an illustration of an embodiment of a control unit display made in accordance with the teachings and principles of the disclosure.

Referring now to FIG. 5 an embodiment of a control unit display 428 that may be part of a control unit 420 will be discussed in greater detail. The display 428 may be a digital display of liquid crystal design (LCD), or the display may be some other technology beside LCD, and may have touch screen functionality and capability for an operator or user to input commands into the system 400. The embodiment discussed herein may have input portions 428a and 428b whereby an operator or user may input commands into the system 400. The embodiment may further comprise a status portion 428c informing a user about the operational status of the components of the system 400. For example, display portion 428c may display an error message related to the condition of an attached imaging device 410 if the imaging device 410 has already been used or has been deemed unfit for a procedure. The display 428 may also have a dedicated message portion 428d providing instructions and further information to an operator or user. The configuration of the display 428 may change during use to accommodate further functionality. A plurality of displays 428 is contemplated by, and falls within the scope of, this disclosure and may be used alternatively or in conjunction with this embodiment. An embodiment may comprise a key pad or a button pad for control purposes within a control unit.

Figure 6:
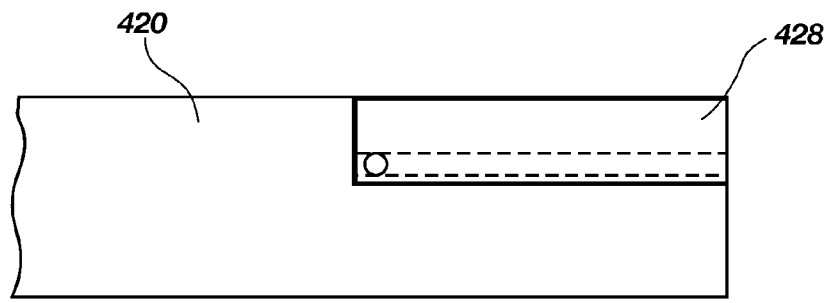
FIG. 6 is an illustration of an embodiment of a retractable display of a control unit in a retracted or closed position and made in accordance with the teachings and principles of the disclosure.
Figure 6A:
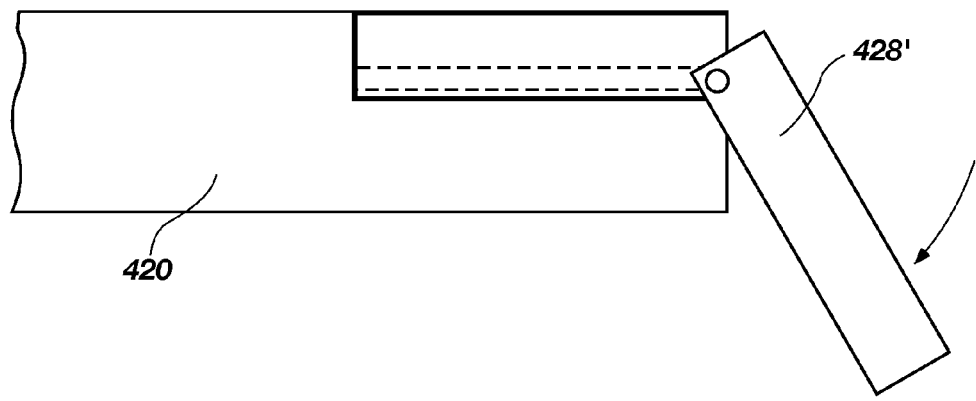
FIG. 6A is an illustration of an embodiment of a retractable display of a control unit in an open position and made in accordance with the teachings and principles of the disclosure.

Illustrated in FIGS. 6 and 6A is an embodiment of a retractable display 428 of a control unit 420. The display 428 may have a first or retracted position within the control unit 420 (illustrated best in FIG. 6) that may be used to protect the display 428 when it is not being used. The display 428' of FIG. 6A illustrates how the display may be deployed into a more user readable position, as it has been extended and rotated outward. As illustrated in FIGS. 6 and 6A, the display may be slid in and out of a passage and rotated about an axis to orient the display 428 in a wide range of positions.

Figure 7:
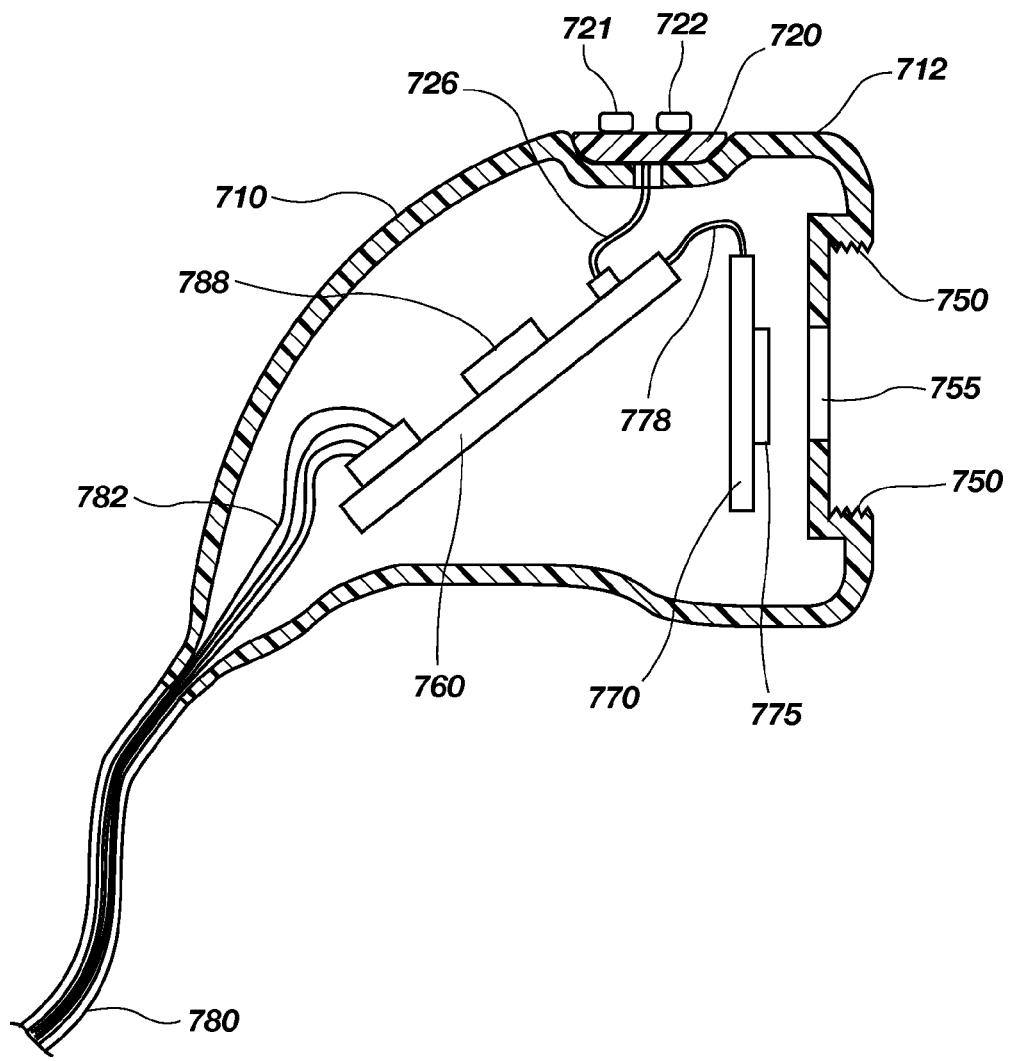
FIG. 7 is a cross-sectional view of an embodiment of an imaging device head made in accordance with the teachings and principles of the disclosure.

Illustrated in FIG. 7 is a cross-sectional view of an embodiment of an imaging device head 712. The imaging device head 712 may comprise a housing 710 made of a suitably rigid material, such as plastic or metal. The housing 710 may be sealed against fluids and gases so as to protect the internal circuitry and provide a suitable surface for sterilization and renewal. The imaging device head 712 may further comprise a user input panel 720 having buttons 721 and 722 for operation of the imaging device head 712. Additional, buttons may be provided and the functionality of the buttons can be customized for a given procedure or a given operator. The control panel 720 may be internally connected to other circuitry of the imaging device head 712 by an electrical connector 726.

As illustrated further in FIG. 7, imaging device head 712 may comprise an optical mount system 750, such as a C-mount system for receiving threaded accessories, for example one inch threaded accessories. A window 755 may also be incorporated into the embodiment for facilitating the transmission of light from an optical accessory to an image sensor 775. The image sensor 775 may be mounted to a supporting printed circuit board or supportive substrate 770. An electronic connector 778 may be incorporated to electronically connect the image sensor 775 to a main circuit or main printed circuit board 760. A main wiring harness 782 may be incorporated into a wired tether 780 thereby electrically connecting the components of the imaging device head 712 to a control unit.

The imaging device head 712 may further comprise a memory 788 or memory circuit allowing the storage of data within the imaging device head 712. It will be appreciated that memory may be any data storage device that is capable of recording (storing) information (data). Data that may be stored or written into memory 788 may include an identifying serial number that uniquely identifies an imaging device. Other data that may be stored or written into memory 788 may include data such as the amount of the time the imaging device has been used, i.e., the hours of operation, or the amount of time the imaging device has been powered on. Data that may be written into memory 788 may include sterilization data or renewal data, representing the working condition of the imaging device. Data that may be stored or written into memory 788 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 788 maybe encryption protected so as to avoid tampering or unintended use. It should be noted that a memory 788 may be placed anywhere in the imaging device and not just the imaging device head without departing from the scope of the disclosure. The memory 788 may comprise a permanent or semi-permanent portion allowing varying degrees of data durability.

Figure 8:
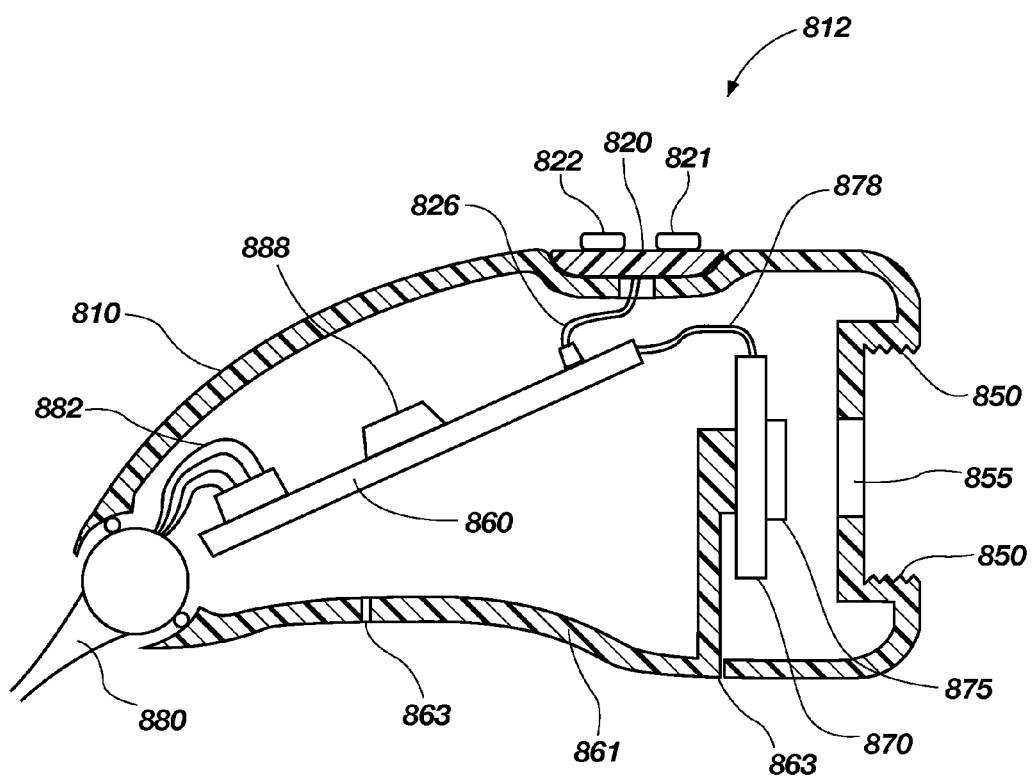
FIG. 8 is a cross-sectional view of an embodiment of an imaging device head made in accordance with the teachings and principles of the disclosure.

Illustrated in FIG. 8 is a cross-sectional view of an embodiment of an imaging device head 812. The imaging device head 812 may comprise a housing 810 made of a suitably rigid material such as plastic or metal. The housing 810 may be sealed against fluids and gases so as to protect the internal circuitry and provide a suitable surface for sterilization and renewal. The imaging device head 812 may further comprise a user input panel 820 having buttons 821 and 822. Additional, buttons may be provided and the functionality of the buttons can be customized for a given procedure and or a given operator. The control panel 820 may be internally connected to other circuitry of the imaging device head 812 by an electrical connector 826.

As illustrated further in the embodiment of FIG. 8, the imaging device head 812 may comprise an optical mount system 850, such as a C-mount system for receiving threaded accessories, for example one inch threaded accessories. A window 855 may also be incorporated into the embodiment for facilitating the transmission of light from an optical accessory to an image sensor 875. The image sensor 875 may be mounted to a supporting printed circuit board or supportive substrate 870. An electronic connector 878 may be incorporated to electronically connect the image sensor 875 to amain circuit or main printed circuit board 860. In order to provide heat dissipation from the image sensor 875 and other circuitry, a heat sink 861 may be provided. The heat sink 861 may be physically connected to the image sensor 875 and it may also be connected to the housing 810, such that heat energy can be conducted or transferred to the external portion of the imaging device head 812. The heat sink 861 may be a neutral sensor heat sink exposed externally to ensure the camera head meets cardiac floating (CF) and body floating (BF) ISO standards. An embodiment of the heat sink 861 may be made of aluminum and have fins for added heat transfer surface area. A main wiring harness 882 may be incorporated into a wired tether 880 thereby electrically connecting the components of the imaging device head 812 to a control unit.

The imaging device head 812 may further comprise a memory 888 or memory circuit allowing the storage of data within the imaging device head 812. Data that may be stored or written into memory 888 may include an identifying serial number that uniquely identifies an imaging device. Other data that may be stored or written into memory 888 may include data such as the amount of the time the imaging device has been used, i.e., the hours of operation, or the amount of time the imaging device has been powered on. Data that may be written into memory 888 may include sterilization data or renewal data, representing the working condition of the imaging device. Data that may be stored or written into memory 888 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 888 may be encryption protected so as to avoid tampering or unintended use. It should be noted that a memory may be placed anywhere in the imaging device and not just the imaging device head without departing from the scope of the disclosure. The memory 888 may comprise a permanent or semi-permanent portion allowing varying degrees of data durability.

Figure 9:
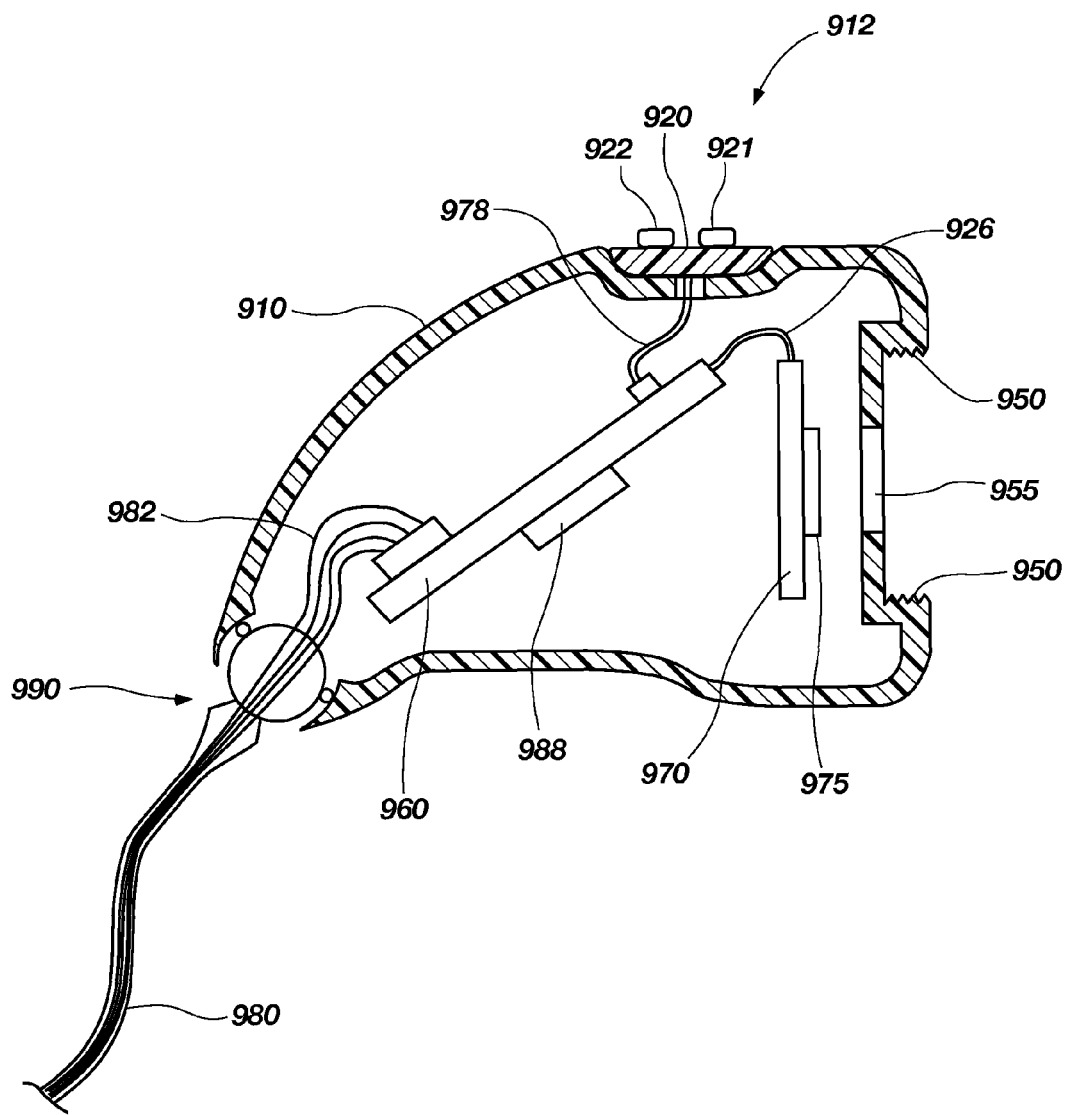
FIG. 9 is a cross-sectional view of an embodiment of an imaging device head made in accordance with the teachings and principles of the disclosure.

Illustrated in FIG. 9 is a cross-sectional view of an embodiment of an imaging device head 912. The imaging device head 912 may comprise a housing 910 made of a suitably rigid material such as plastic or metal. The housing 910 may be sealed against fluids and gases so as to protect the internal circuitry and provide a suitable surface for sterilization and renewal. The imaging device head 912 may further comprise a user input panel 920 having buttons 921 and 922. Additional, buttons maybe provided and the functionality of the buttons can be customized for a given procedure and or a given operator. The control panel 920 may be internally connected to other circuitry of the imaging device head 912 by an electrical connector 926.

As illustrated further in the embodiment of FIG. 9, the imaging device head 912 may comprise an optical mount system 950, such as a C-mount system for receiving threaded accessories, for example one inch threaded accessories. A window 955 may also be incorporated into the embodiment for facilitating the transmission of light from an optical accessory to an image sensor 975. The image sensor 975 may be mounted to a supporting printed circuit board or supportive substrate 970. An electronic connector 978 may be incorporated to electronically connect the image sensor 975 to a main circuit or main printed circuit board 960. In order to provide heat dissipation from the image sensor 975 and other circuitry, a heat sink may be provided, similar to the heat sink provided in FIG. 8. The heat sink may be physically connected to the image sensor 975 and it may also be connected to the housing 910, such that heat energy can be conducted or transferred to the external portion of the imaging device head 912. A main wiring harness 982 may be incorporated into a wired tether 980 thereby electrically connecting the components of the imaging device head 912 to a control unit.

The imaging device head 912 may further comprise a memory 988 or memory circuit allowing the storage of data within the imaging device head 912. Data that may be stored or written into memory 988 may include an identifying serial number that uniquely identifies an imaging device. Other data that may be stored or written into memory 988 may include data such as the amount of the time the imaging device has been used, i.e., the hours of operation, or the amount of time the imaging device has been powered on. Data that may be stored or written into memory 988 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 988 may be encryption protected so as to avoid tampering or unintended use. It should be noted that a memory may be placed anywhere in the imaging device and not just the imaging device head without departing from the scope of the disclosure. The memory 988 may comprise a permanent or semi-permanent portion allowing varying degrees of data durability.

The imaging device head 912 may comprise a ball joint 990 with a corresponding seal and socket, thereby providing increased mobility between the housing 910 and the tether 980 during articulation of the imaging device by an operator or user.

Figure 10:
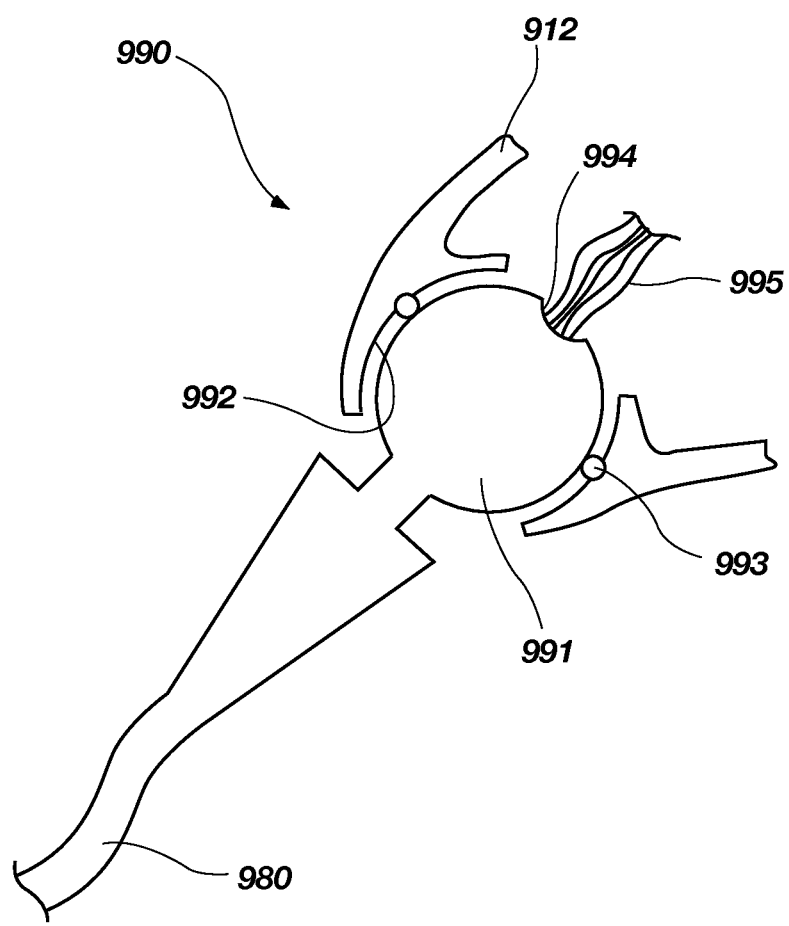
FIG. 10 is a cross-sectional view of an embodiment of an imaging device head having a ball joint made in accordance with the teachings and principles of the disclosure.

With reference primarily to FIG. 10, an embodiment of an imaging device ball joint 990 will be discussed in further detail. FIG. 10 is illustrative of a cross-sectional view of a ball joint 990, which provides greater freedom of articulation for an operator when moving the imaging device head 912 relative to the wiring tether 980. The ball joint 990 may comprise a substantially spherical rotatable portion or ball 991. The ball 991 may be configured to mechanically operate in communication with a corresponding socket 992, such that the ball 991 may substantially freely rotate while being retained within the socket 992. A seal may be provided withing the ball joint 990 by the inclusion of a seal ring 993. The seal ring 993 may also provide mechanical resistence within the ball joint 990. The ball 991 may further include an opening 994 therethrough allowing wiring 995 to pass through the ball joint 990.

Figure 11:
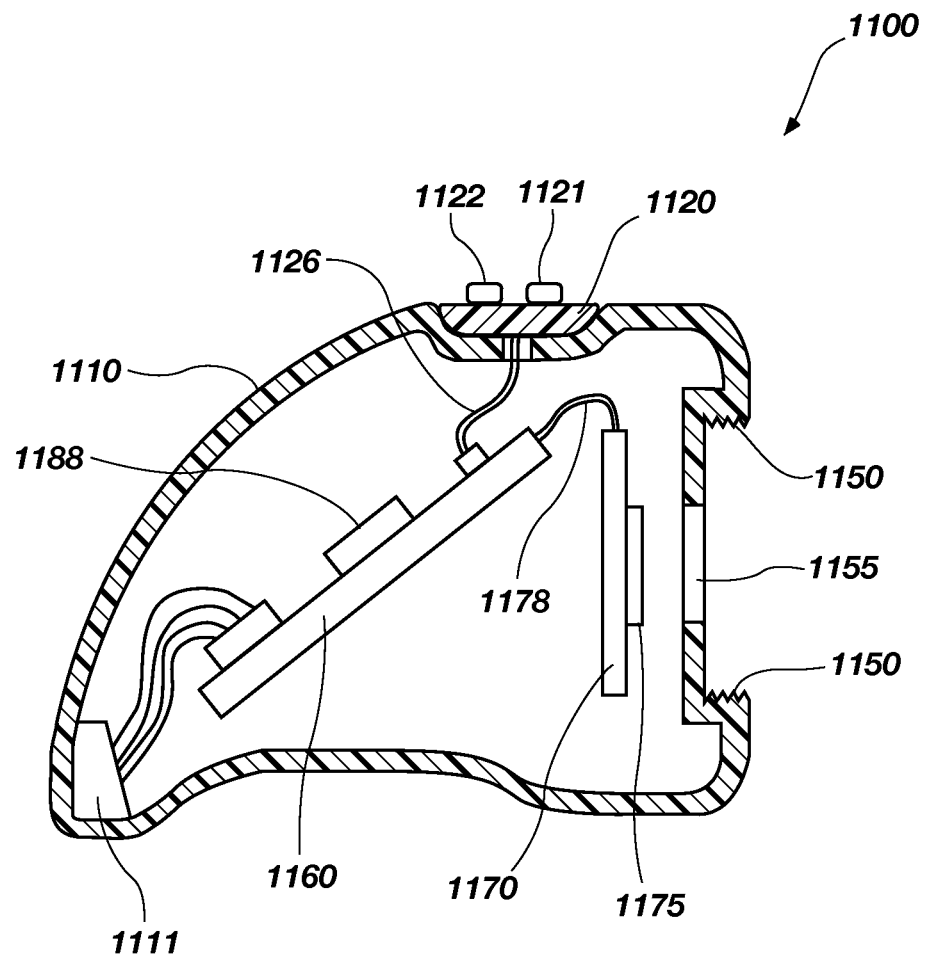
FIG. 11 is a cross-sectional view of an embodiment of an imaging device head made in accordance with the teachings and principles of the disclosure.

With reference to FIG. 11, an embodiment of an imaging device 1100 comprising wireless transmission functionality will be discussed. A cross-sectional view of an embodiment of an imaging device head 1112 is shown in FIG. 11. The imaging device head 1112 may comprise a housing 1110 made of a suitably rigid material such as plastic or metal. The housing 1110 may be sealed against fluids and gases so as to protect the internal circuitry and provide a suitable surface for sterilization and renewal. The imaging device head 1112 may further comprise a user input panel 1120 having buttons 1121 and 1122. Additional, buttons may be provided and the functionality of the buttons can be customized for a given procedure and or a given operator. The control panel 1120 may be internally connected to other circuitry of the imaging device head 1112 by an electrical connector 1126. The imaging device head 1112 may communicate with a control unit by way of wireless transmissions such as Wifi, infrared, bluetooth etc. Other forms of wireless non-tethered connectivity may also be used for providing communication between the imaging device head 1112 and the control unit, including but not limited to, radio frequency from any available spectrum, infrared of any configuration, ultrasonic, and optical. As illustrated further in the embodiment of FIG. 11, the imaging device head 1112 may comprise an optical mount system 1150, such as a C-mount system for receiving threaded accessories, for example one inch threaded accessories. A window 1155 may also be incorporated into the embodiment for facilitating the transmission of light from an optical accessory to an image sensor 1175. The image sensor 1175 may be mounted to a supporting printed circuit board or supportive substrate 1170. An electronic connector 1178 may be incorporated to electronically connect the image sensor 1175 to a main circuit or main printed circuit board 1160. The circuitry of the imaging device head 1112 may electrically be connected to a wireless transceiver 1111 for transmitting and receiving data from a wirelessly configured control unit as illustrated in FIG. 3.

The imaging device head 1112 may further comprise a memory 1188 or memory circuit allowing the storage of data within the imaging device head 1112. Data that may be stored or written into memory 1188 may include an identifying serial number that uniquely identifies an imaging device. Other data that may be stored or written into memory 1188 may include data such as the amount of the time the imaging device has been used, i.e., the hours of operation, or the amount of time the imaging device has been powered on. Data that may be stored or written into memory 1188 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 1188 may be encryption protected so as to avoid tampering or unintended use. It should be noted that a memory may be placed anywhere in the imaging device and not just the imaging device head without departing from the scope of the disclosure. The memory 1188 may comprise a permanent or semi-permanent portion allowing a varying degrees of data durability.

It will be appreciated that the ball joint illustrated in FIGS. 9 and 10 may be used by any embodiment of the disclosure without departing from the spirit or scope of the disclosure. Thus, for example, the ball joint 990 may be used with imaging device head 712, 812, 912, or 1112. Similarly, it will be appreciated that the heat sink 861 (illustrated in FIG. 8) may be used by any embodiment of the disclosure without departing from the scope of the disclosure.

Figure 12:
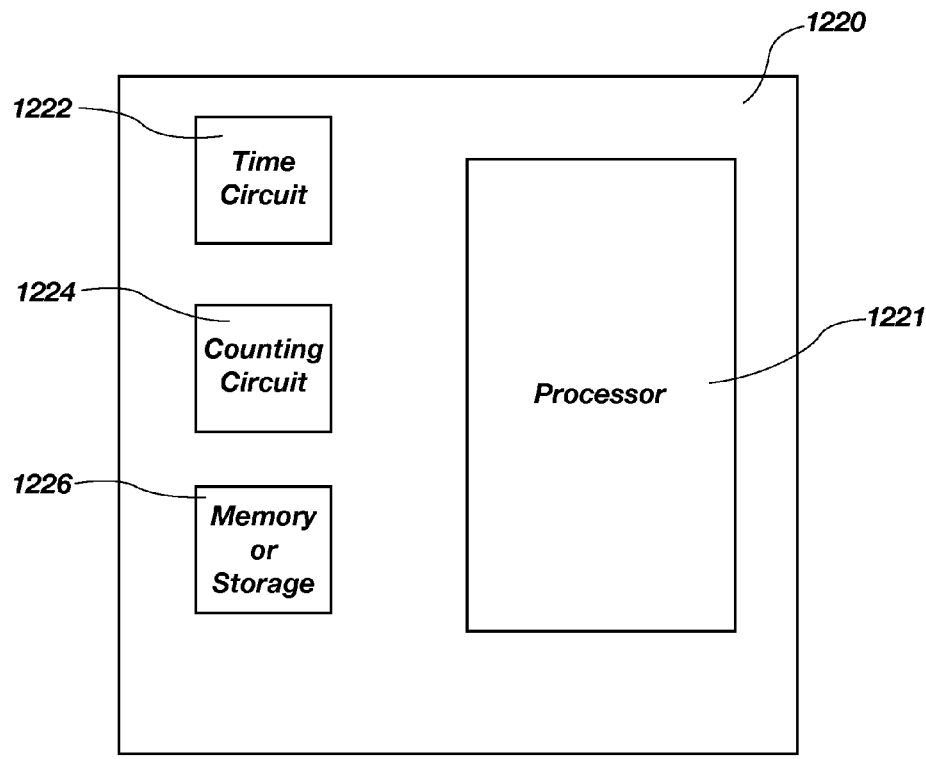
FIG. 12 is a layout view of an embodiment of an imaging system made in accordance with the teachings and principles of the disclosure.
Figure 12:
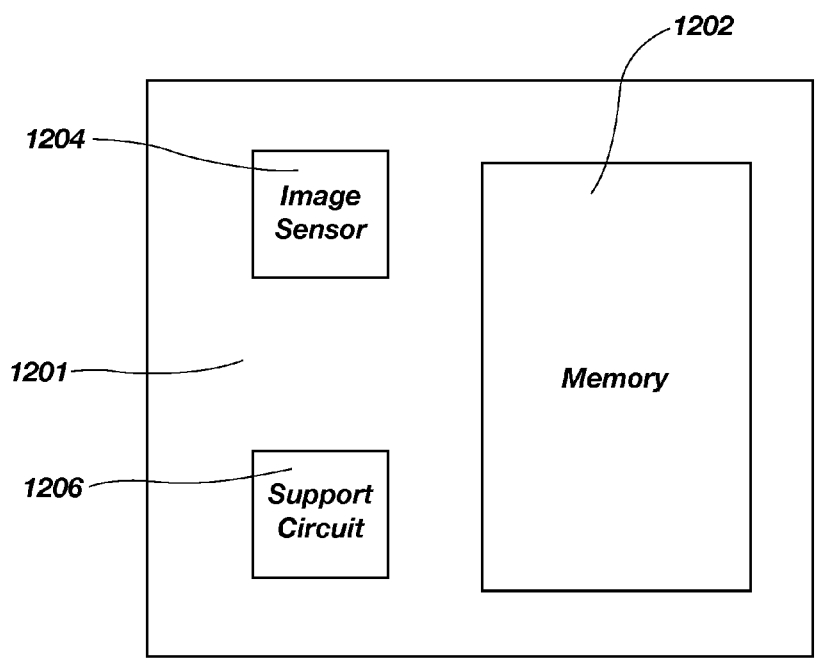

Referring now to FIG. 12 an embodiment of a system for acquiring imagery in a sterilized environment will be discussed. The system may comprise an imaging device 1201 having a memory 1202, an image sensor 1204, and supporting circuitry 1206. The system may further comprise and control unit 1220 having a processor 1221, time circuit or realtime clock 1222, a counting or incrementing circuit 1224 and a control unit memory 1226. The components will generally be provided in a housing, but are shown hear in block diagram form for simplicity and discussion purposes. It is contemplated that any of the above circuits can operate from either a control unit or an imaging device.

Figure 13:
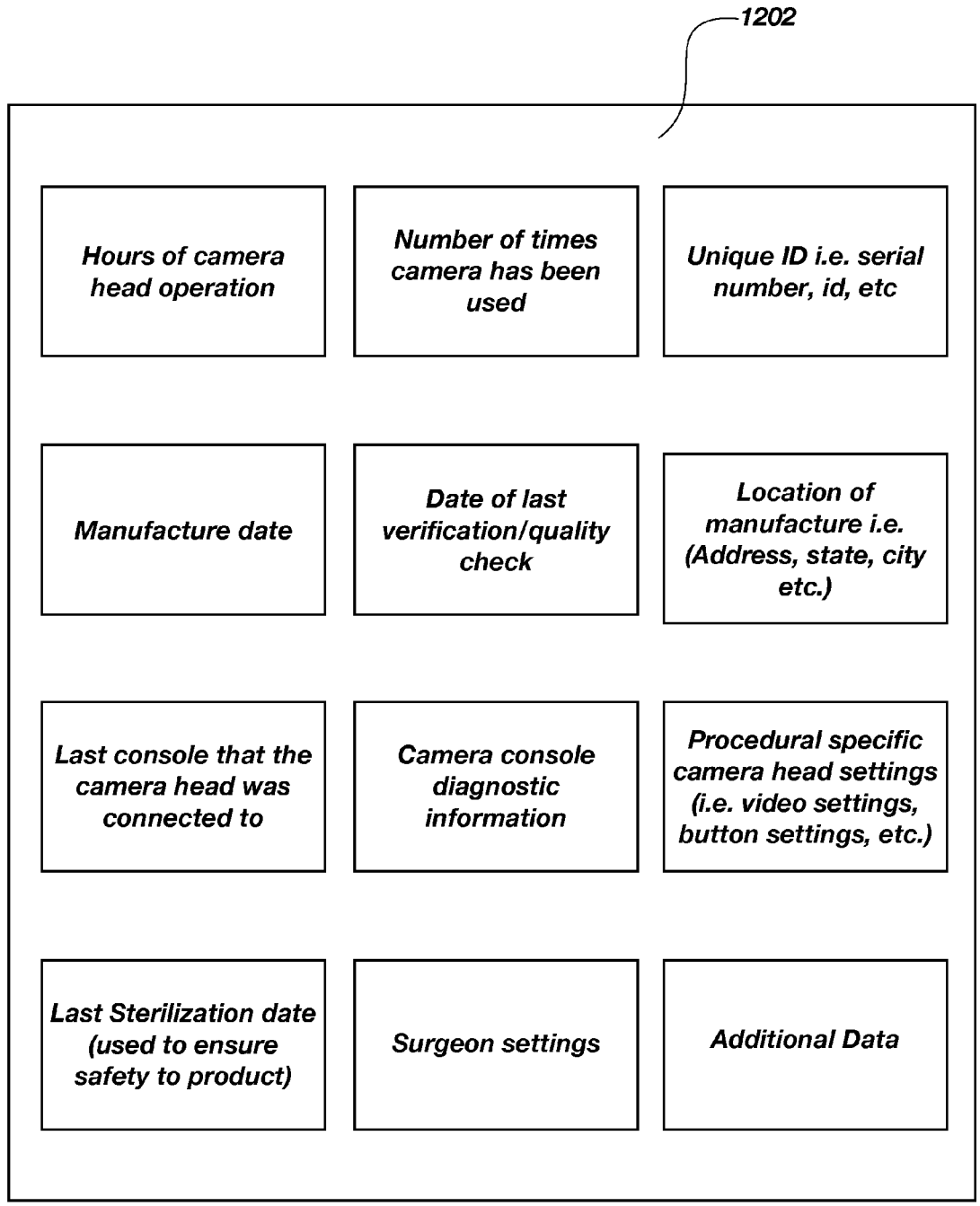
FIG. 13 is a schematic diagram of a memory of an embodiment of an imaging system made in accordance with the teachings and principles of the disclosure.

As can be seen in FIG. 13 the memory 1202 of the imaging device 1201 may comprise the following arrays of data storage:
a. Hours of camera head operation;
b. Number of times camera has been used;
c. Unique identification i.e. serial number, id, etc.;
d. Manufacture date;
e. Date of last verification/quality check;
f. Location of manufacture i.e. (Address, state, city etc.);
g. Last console that the camera head was connected to;
h. Camera console diagnostic information;
i. Procedural specific camera head settings (i.e. video settings, button settings, etc.);
j. Last Sterilization date (used to ensure safety to product); and
k. Surgeon settings.
Additional data may be stored within the memory 1202 that would enhance the imaging device and is considered to be within the scope of the disclosure.

Figure 14:
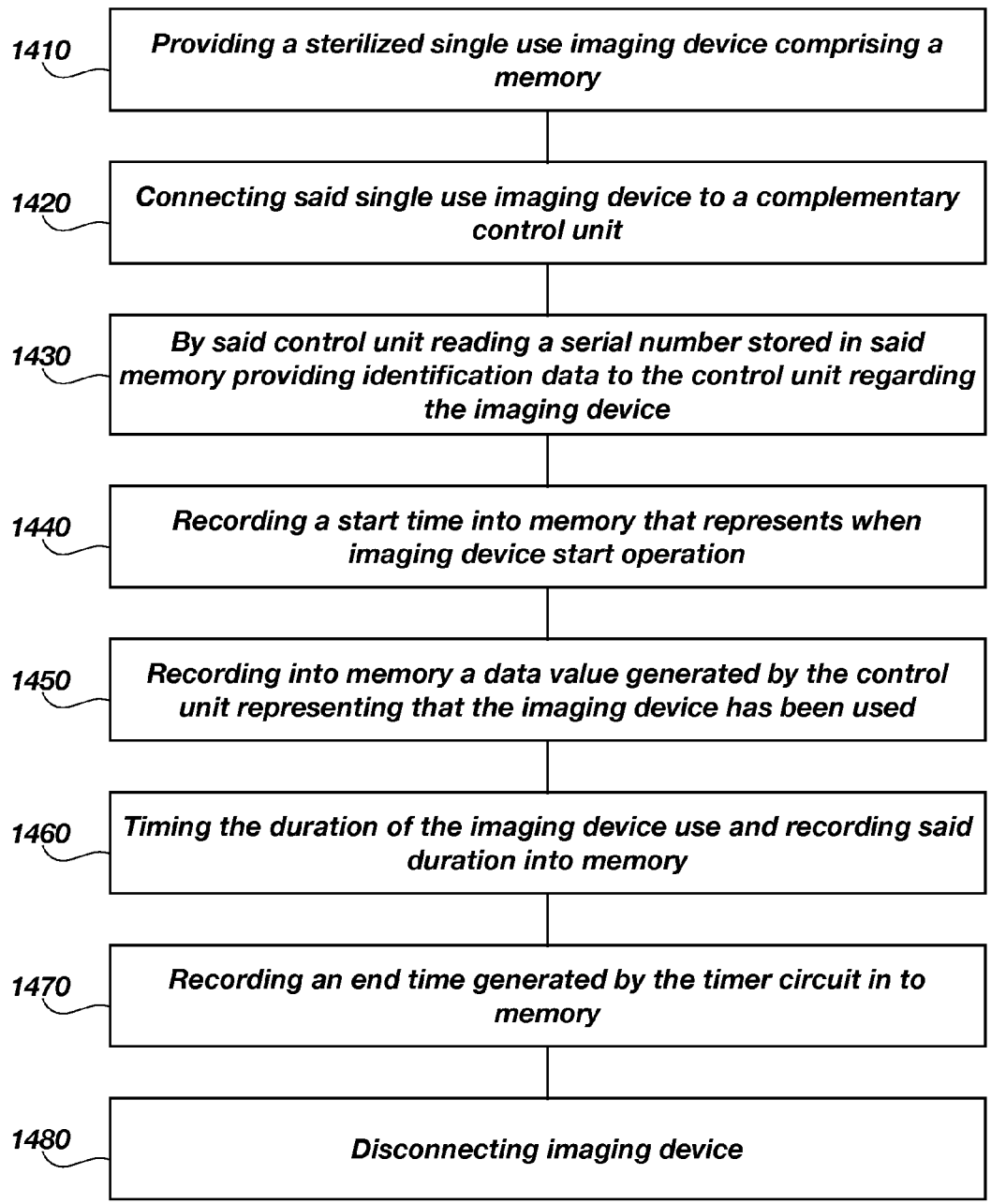
FIG. 14 illustrates an embodiment of a method in accordance with the teachings and principles of the disclosure.

With reference to FIG. 14, a method of using an imaging system consistent with the embodiments disclosed herein will be discussed. In use, a sterilized single use imaging device 1201 will be provided that may comprise memory 1202 at 1410. At 1420 a user may connect the single use imaging device 1201 to a complementary control unit 1220 both electronically and physically. At 1430 the control unit 1220 may initiate a process of reading memory 1202 and registers the serial number of the imaging device 1201. At 1440 the system causes a value to be recorded into memory 1202 indicating that the imaging device 1201 has been used. At 1450 the system records into memory 1202 the date and time the imaging device 1201 is connected to the control unit 1220. At 1460 a timing process is initiated by the control unit from the base line time recorded at 1450 and tracks or times the duration that the imaging device 1201 is used and the duration is recorded into memory 1202 at 1470. After use, the imaging device 1201 is disconnected from the control unit 1220 at 1480 and then discarded for renewal or reclamation.

Figure 15:
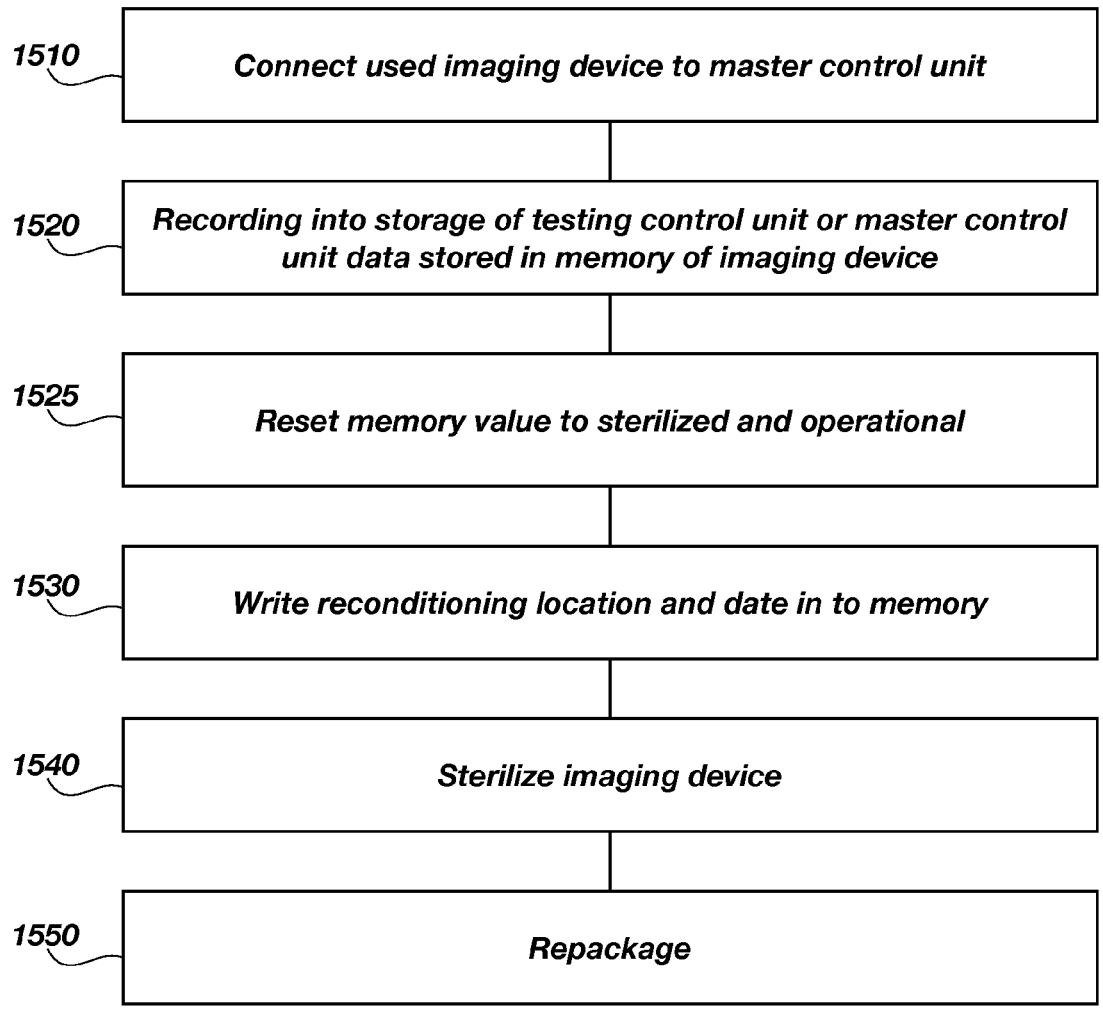
FIG. 15 illustrates an embodiment of a method in accordance with the teachings and principles of the disclosure.

Referring now to FIG. 15, a method of renewing and reclaiming a single use imaging device 1201 will be discussed. At 1510 the imaging device 1201 may be connected to a testing control unit or a master control unit. At 1520 the testing control unit or master control unit causes the data stored in memory 1202 to be recorded into storage on the testing control unit or master control unit as stored, in order for the specific imaging device 1201 to be renewed. At 1525 a value is placed in memory 1202 indicating that the imaging device has been renewed and is ready for use such that when connected to another control unit for use it will operate. The location and date of the renewal may then be recorded into memory 1202 at 1530. At 1540 the imaging device 1201 can be sterilized and (at 1550) placed in a protective sterilized package.

Figure 16:
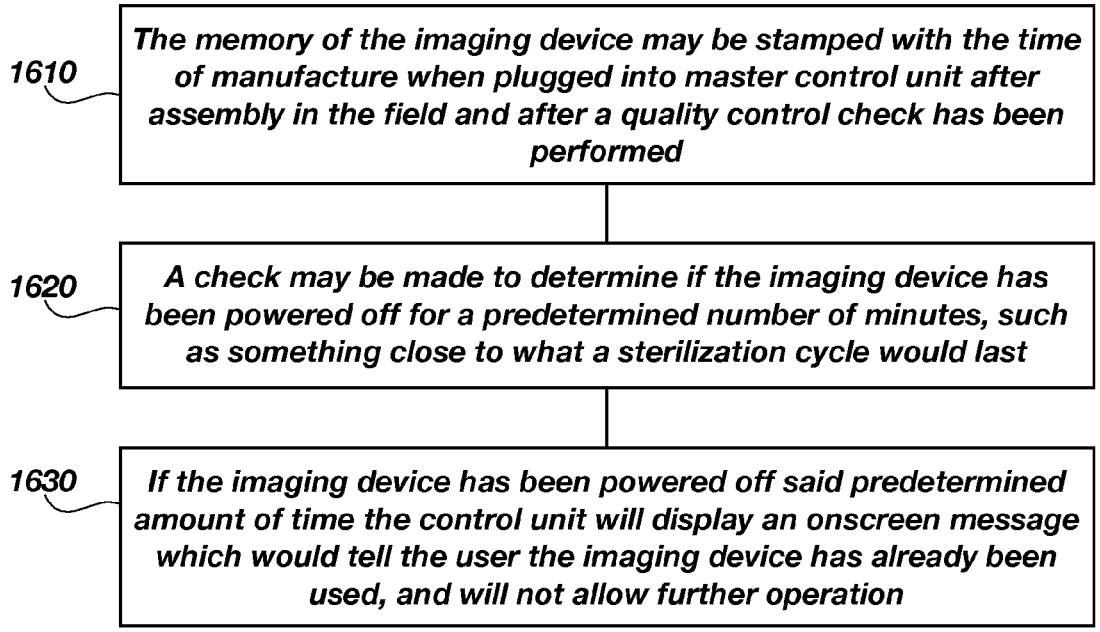
FIG. 16 illustrates an embodiment of a method in accordance with the teachings and principles of the disclosure.

With reference to FIG. 16 an alternative embodiment of a method of use will be discussed illustrating safety settings of the embodiment. At 1610 the memory imaging device head may be stamped with time of manufacture when it is plugged into the master control unit or master console after assembly in the field, i.e., in an operating room, and after a quality control check has been performed. At 1620 a check may be made to determine if the imaging device has been powered off for a predetermined number of minutes, such as a time frame that is close to what a typical sterilization cycle would last. At 1630, if the imaging device has been powered off the predetermined amount of time the control unit will display an onscreen message telling the user the imaging device has already been used, and will not allow further operation, such that no image will be produced through video feed. This feature will ensure the imaging device, i.e., the camera, will not be used more than one time per sterilization cycle. This feature also protects the patient and the doctor from an invalid or unsafe use.

Figure 17:
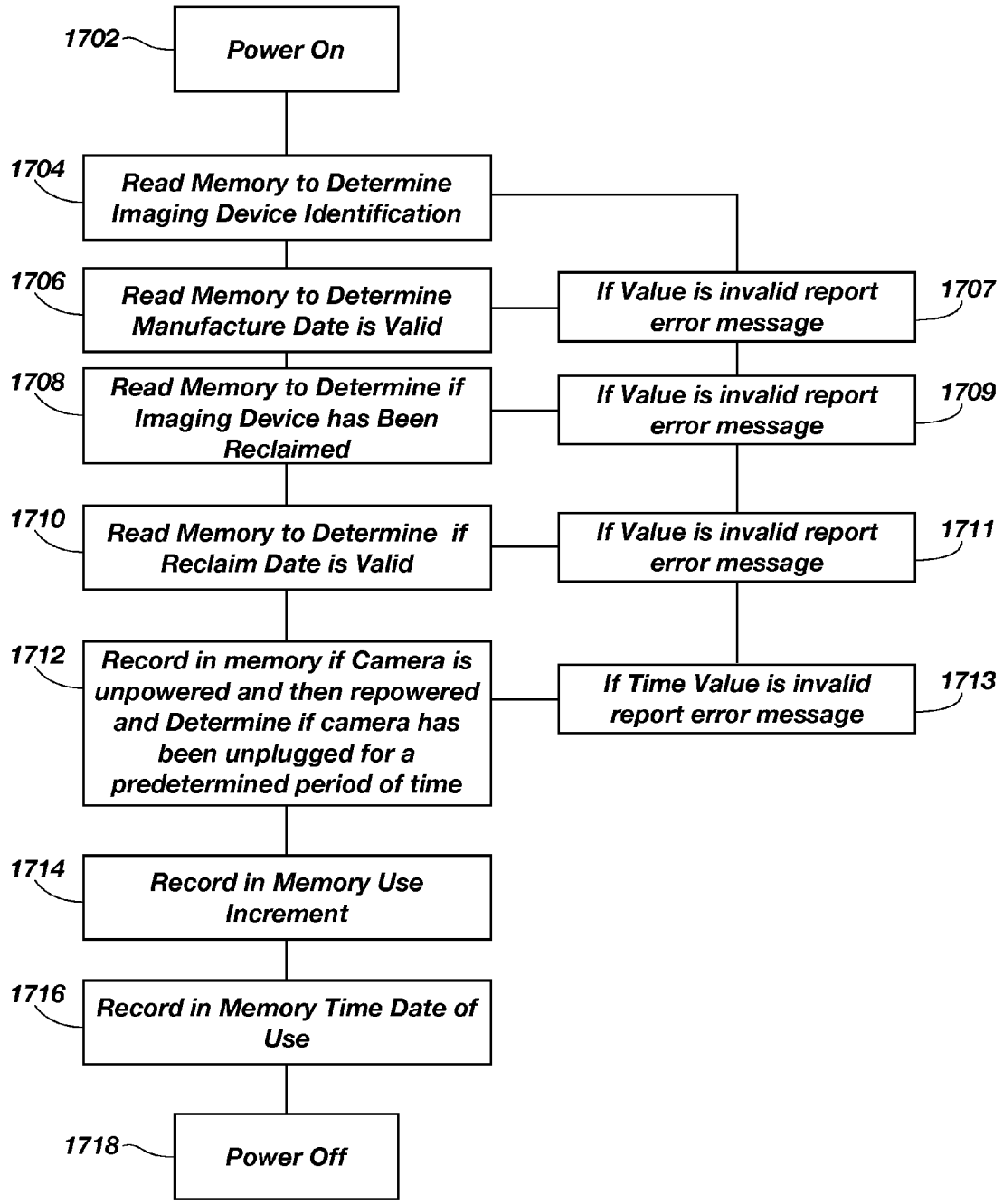
FIG. 17 illustrates an embodiment of a method of use according to the teachings and principles of the disclosure.

Referring to FIG. 17 an embodiment of a method of use will be discussed. During use, an imaging device may be connected to a control unit. Upon connection, an electronic communication connection is formed between the imaging device and the control unit. At 1702 the imaging device may be powered on by power supplied by the control unit. At 1704 a processor in the control unit may cause data regarding imaging device identification that may be stored in a memory within the imaging device to be read. At 1706 a processor in the control unit may cause data regarding the manufacturing date of the imaging device to be read from memory within the imaging device. The processor in the control unit may then compare the data to a predetermined data value range. At 1707 an error message may be displayed if the read data is outside the predetermined data value range and the imaging device will be stopped from operating. At 1708 a processor in the control unit may cause data regarding the reclamation of the imaging device to be read from memory within the imaging device. The data regarding reclamation of the imaging device may include data representing whether or not the imaging device has been previously used. The processor may then compare the data to a predetermined data value range. At 1709 an error massage may be displayed if the read data is outside the predetermined data value range and the imaging device will be stopped from operating. At 1710 a processor in the control unit may cause data regarding the reclamation date of the imaging device to be read from memory within the imaging device. The processor may then compare the data to a predetermined data value range. At 1711 an error massage may be displayed if the read data is outside the predetermined data value range and the imaging device will be stopped from operating. At 1712 a processor in the control unit may cause usage information of the current procedure to be monitored to note whether imaging device has been unpowered for a predetermined period of time and then re-powered. If this condition occurs it is possible that the imaging device has been tampered with or that an attempt has been made to sterilize the imaging device and use it a second time. The predetermined period of time may correspond to the amount of time a typical sterilization process would normally take. The processor then compares the data to a predetermined data value range. At 17013 an error massage may be displayed if the data read is outside the predetermined data value range and the imaging device will be stopped from operating. At 1714 a processor in the control unit may cause a value to be placed in memory in the imaging device indicating that the imaging device has been used. At 1716 a processor in the control unit may cause the date and time of use to be recorded in memory in the imaging device. Additional information may be recorded into the memory of the imaging device such as, for example, duration of use, procedure settings, and user settings and any other data suitable for recording to memory. The imaging device may be disconnected from the control unit and thereby powered off at 1718.

Figure 18:
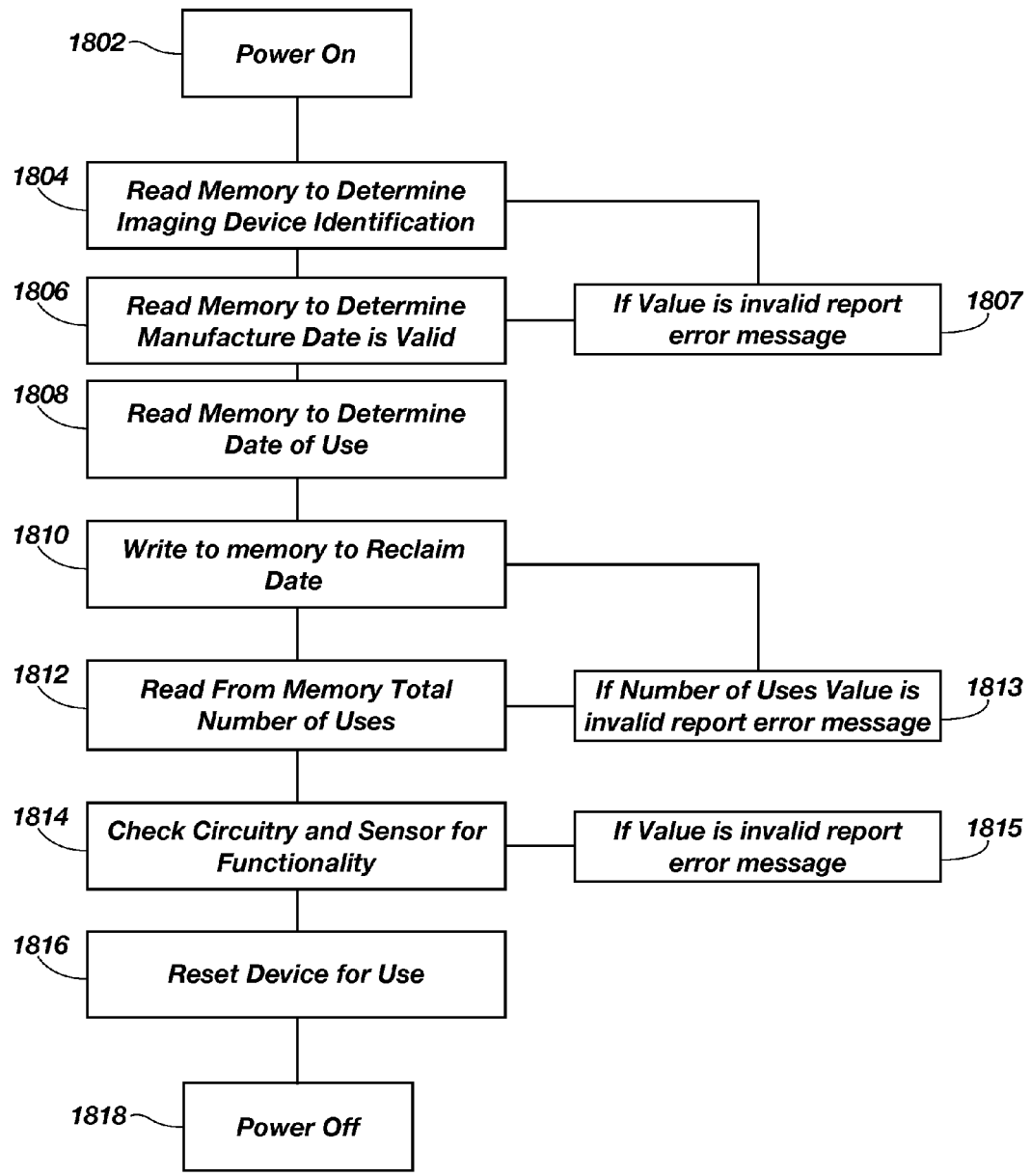
FIG. 18 illustrates an embodiment of a method of reclaiming an imaging device after use according to the teachings and principles of the disclosure.

Referring now to FIG. 18 a method of reclaiming an image device after use will be discussed. It should be noted that a single use imaging device may comprise the durability to be used a plurality of times, however sterilization requirements may prevent an imaging device from being used more than once without a process for reclaiming the imaging device, thereby returning it to a sterilized condition. A method of reclamation for an imaging device may comprise the process of powering on the imaging device at 1802, when the imaging device is electrically connected to a control unit. At 1804 a processor in the control unit may cause data representing identification information for the imaging device to be stored in storage in the control unit. A control unit may be a master control unit configured for reclaiming the imaging devices. The master control unit may track a plurality of imaging devices thereby keeping a catalog of associated information such as use and condition of the device or devices. At 1806 a processor in the control unit may cause that data representing a manufacturing date to be read and compared to a predetermined value or range of values. If the read data is out of the predetermined range value, an error report may be issued at 1807. At 1808 a processor in the control unit may cause data representing use data written in memory of the imaging device to be read and recorded into storage in the control unit. At 1810 a processor may cause data representing a date and time of reclamation to be recorded into memory in the imaging device. At 1812 a processor in the control unit may cause that data representing the number of uses of the imaging device to be read and recorded into storage in the control unit. The processor may compare the read data to a predetermined value or range of values to determine whether the imaging device is fit for continued use. If the predetermined value is exceeded an error message may be displayed (at 1813) and the imaging device may be retired. At 1814 a processor in the control unit may initiate a test or quality control check of all the circuitry in the imaging device to ensure that the device is functional. At 1815 it may be determined that the imaging device failed the quality control check and an error massage may be displayed. At 1816 the imaging device can be reset for use. The resetting process may comprise writing data to the memory of the imaging device indicating that the imaging device has been reclaimed and sterilized. At 1816 the device may be disconnected from the control unit and physically sterilized and repackaged.

Figure 19:
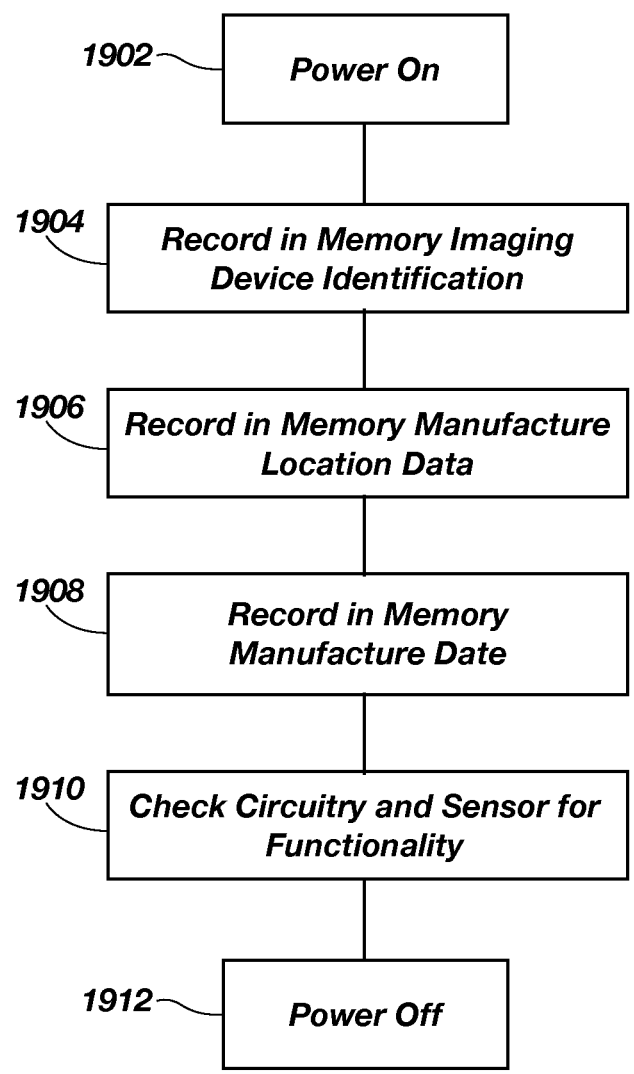
FIG. 19 illustrates an embodiment of a method of making an imaging device for use in a sterilized environment according to the teachings and principles of the disclosure.

With reference primarily to FIG. 19 an embodiment of a method for making an imaging device having memory therein for use in a sterilized environment will be discussed. At 1902 an imaging device may be powered on upon being connected to a control unit. The control unit may be a master control unit configured for the manufacturing process. At 1904 a processor in the control unit may cause that data representing an identification serial number for the imaging device to be written into memory of the imaging device. At 1906 a processor in the control unit may cause that data representing the location of manufacture be recorded to memory in the imaging device. At 1908 a processor may cause that data representing the date of manufacture may be recorded into memory on the imaging device. At 1910 a processor in the control unit may initiate a test or quality control check of all the circuitry in the imaging device to ensure that the device is functional. At 1912 the imaging device may be unplugged from the control and sterilized for packaging.

Figure 20:
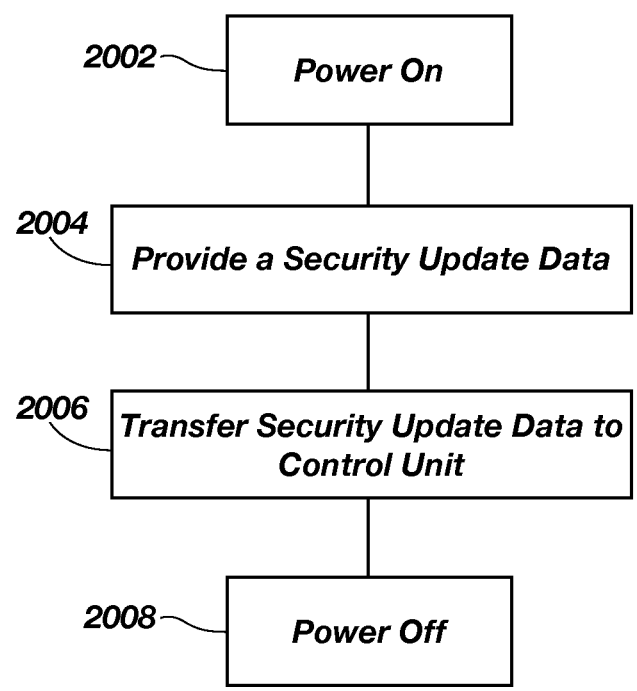
FIG. 20 illustrates an embodiment of a method for updating an imaging device system.

Referring to an embodiment illustrated in FIG. 20, a system having a security code or some other means of identifying, and validating for use, an imaging device by a control unit, in order to verify that the imaging device is authorized for use will now be described. A validating security code or procedure of validation may be distributed to control units from a central database over the internet, by direct transfer from portable storage device such as USB device containing memory, another computer, or other storage device. With reference to FIG. 20 an embodiment of a method for providing updates with in a medical imaging system will be discussed. At 2002 a control unit may be powered on to receive a security update. At 2004 security update data may provided comprising validation codes that correspond to imaging devices to be connected to the control unit. Such validation codes may enable the system to insure that users of the system may be prevented from using imaging devices that have been selected for non-use by a manufacturer or distributor. Selection criteria for non-use may include safety considerations, recall considerations, anti counterfeit measures, and sales and contract considerations. At 2006 the data may be transferred into storage or memory of the control unit in order to provide that data for later comparison to security codes provided by imaging devices. It is within the scope of this disclosure to include all means for transferring data, including but not limited to, transmission over a network, transfer via on site transmission from a storage medium that is portable, such as a disk, memory drive, or short distance wireless transmission. At 2008 the system may be powered off.

Figure 21:
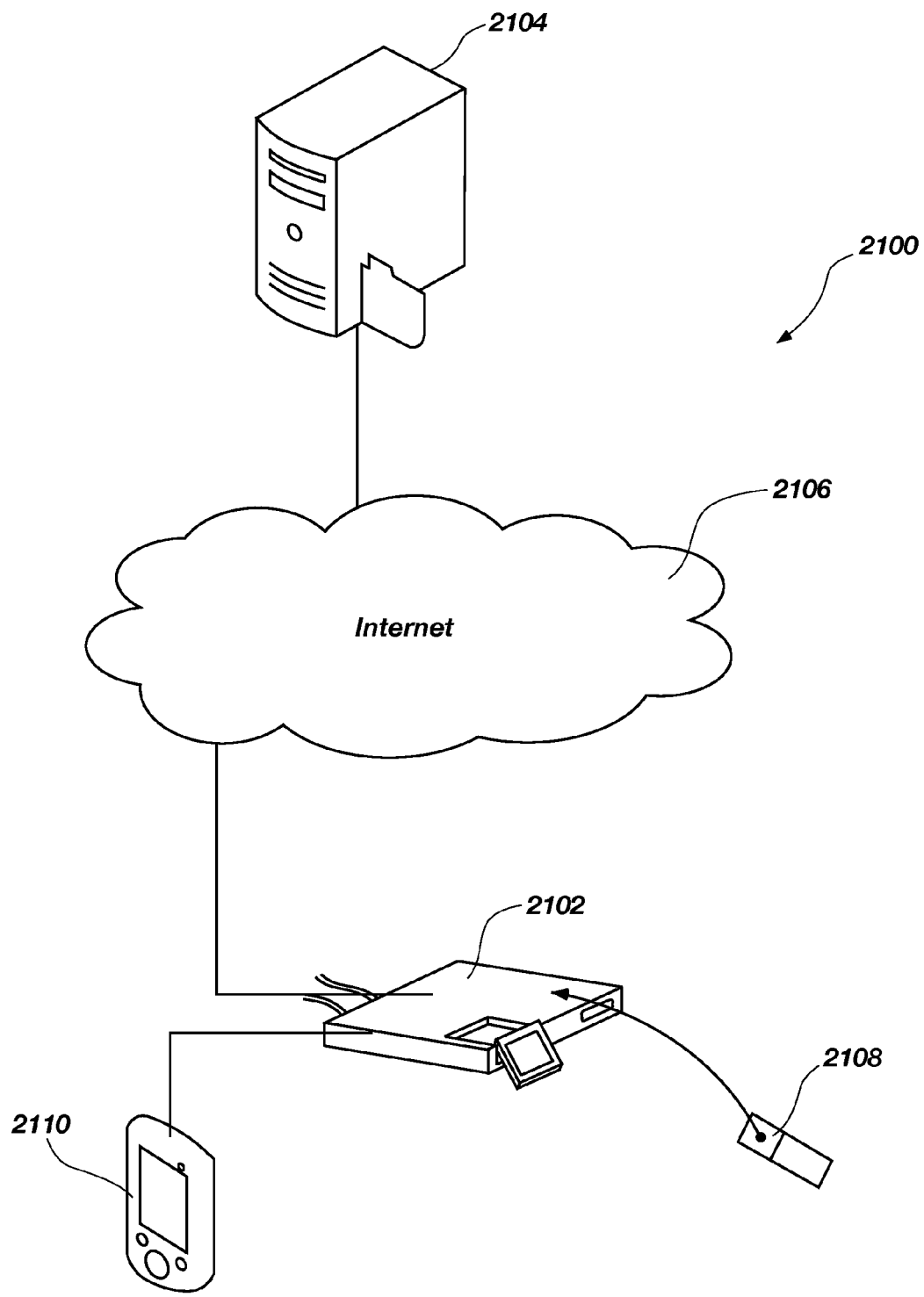
FIG. 21 illustrates an embodiment of a system for providing updates to an imaging system.

With reference primarily to FIG. 21 an embodiment of an imaging system have the feature of updating data will be discussed. An imaging system 2100 may comprise a control unit 2102 and a data server 2104. The control unit 2106 may be electronically in communication with the data server 2104 over a network such as the internet 2106. The control unit 1202 may receive update data over the internet 2106 from data server 2104. The control unit 2102 may also receive update data directly from a memory transfer device 2108 such as a memory stick, thumb drive, jump drive, hard drive, optical disk to name a few. The control unit 2102 may also receive update data from another computer or portable device 2110 such as a PDA or laptop that is presented to the control unit 2102 on site. Data transfer may be made with a physical connection and or by a wireless transfer of data.

In the foregoing Detailed Description, various features of the disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A sterilized single use imaging device comprising:
   a housing;
   an image sensor;
   an optic mount in said housing configured for receiving optics;
   an opening proximate to said optic mount and configured to facilitate transmission of light from said optics to said image sensor;
   a memory comprising data representing characteristics of the imaging device; and
   an electronic communication circuit configured for providing electronic communication between said imaging device and a control unit.

2. The imaging device of claim 1, wherein the imaging device is for use with and communicating with the control unit, wherein the imaging device further comprises a main circuit having the memory thereon.

3. The imaging device of claim 1, wherein data comprising a serial number is stored in said memory for providing identification of the imaging device.

4. The imaging device of claim 1, wherein the imaging device further comprises a counting circuit that is configured to cause a count value to be recorded in said memory circuit for each time the imaging device is used.

5. The imaging device of claim 2, wherein a timing circuit causes a date and time value to be recorded in said memory when the main circuit is powered on and said timing circuit further records the amount of time the imaging device is in use in said memory.

6. The imaging device of claim 1, wherein the imaging device further comprises data comprising the date of the last sterilization recorded in memory.

7. The imaging device of claim 1, wherein the imaging device further comprises user settings that are recorded in memory.

8. The imaging device of claim 1, wherein the imaging device further comprises procedure specific settings that are recorded in memory.

9. The imaging device of claim 1, wherein the imaging device further comprises a location of manufacture data that is recorded in memory.

10. The imaging device of claim 1, wherein the imaging device further comprises a date of manufacture data that is recorded in memory.

11. The imaging device of claim 1, wherein the imaging device further comprises a date of last quality control check that is recorded in memory.

12. The imaging device of claim 1, wherein the imaging device further comprises imaging device diagnostic data for use with a second complimentary apparatus.

13. The imaging device of claim 1, wherein said electronic communication circuit is a tether of wires having an electronic connector configured to mate with a corresponding electronic connector on said control unit.

14. The imaging device of claim 13, wherein said tether of wires comprises a ball configured to mechanically communicate with a corresponding socket structure of said housing.

15. The imaging device of claim 14, further comprising an "O" ring seal disposed about said ball thereby forming a seal between said ball and said corresponding socket.

16. The imaging device of claim 1, wherein said electronic communication circuit is a wireless communication transceiver configured to communicate wirelessly with a corresponding transceiver on said control unit.

17. The imaging device of claim 1, wherein radio frequency identification is used to provide identifying information.

18. The imaging device of claim 1, wherein said imaging device further comprises a heat sink.

19. The imaging device of claim 1, wherein said memory comprises:
   a. data representing the number of hours of operation of the imaging device;
   b. data representing the number of times the imaging device has been used;
   c. data representing a unique identification code;
   d. data representing a date of manufacture;
   e. data representing a date of last verification/quality check;
   f. data representing a location of manufacture;
   g. data representing the last control unit to which the imaging device was connected;
   h. data representing diagnostic information;
   i. data representing procedural specific settings;
   j. data representing a date of last sterilization; or
   k. data representing specific settings for a specific user.

20. The imaging device of claim 19, wherein said memory comprises video settings.

21. The imaging device of claim 19, wherein said memory comprises video control panel settings.

22. A method for providing a single use imaging system for use in sterile environments comprising:
   providing a sterilized single use imaging device comprising a memory and an electronic communication circuit;
   electrically connecting said single use imaging device to a complementary control unit, wherein said electronic communication circuit provides electronic communication between the imaging device and the control unit; and
   recording data into the memory of the single use imaging device, after connection to the control unit, said data representing characteristics of the imaging device.

23. The method of claim 22, wherein the method further comprises:
   recording a start time into memory that represents a first use of the imaging device;
   timing the duration of the imaging device's use; and
   recording an end time into memory.

24. The method of claim 22, wherein the sterilized single use imaging device comprises:

a housing configured for housing the components of the imaging device; a control panel configured to aid an operator in causing features to be actuated;
a mount configured for receiving medical optics;
a timing circuit;
a counting circuit;
a memory circuit; and
an opening proximate to said mount and configured to facilitate the transmission of light from said medical optics to an image sensor.

25. The method of claim 22, wherein said control unit comprises:
an imaging device electronic input;
a user readable control panel;
video outputs; and
video inputs.

26. The method of claim 22, wherein the method further comprises comparing a value to a predetermined parameter and if said value is outside of the parameter the imaging device will return an error message and will not operate.

27. The method of claim 22, wherein the method further comprises comparing a count value generated by the control unit and stored in memory to a predetermined parameter and if said count value is within the parameter the imaging device will return a message and will operate.

28. The method of claim 22, wherein the method further comprises comparing the amount of time the single use imaging device has been in operation to a predetermined parameter and if the amount of time the imaging device has been in use is outside of the parameter the imaging device will return an error message and will not operate.

29. The method of claim 22, wherein a date of manufacture of the imaging device is stored in the memory and read by the control unit.

30. The method of claim 29, wherein the control unit reads the date of manufacture from memory and compares that date of manufacture to a predetermined date and if said date of manufacture is beyond the predetermined date the imaging device will not operate and a message will be displayed to the operator.

31. The method of claim 22, wherein the method further comprises reading whether the imaging device has been used, and verifying the sterility of the imaging device by reading a date of packaging stored in memory.

32. The method of claim 31, wherein the control unit reads the date of packaging read from memory and compares the date of packaging to a predetermined date and if said date of packaging is beyond the predetermined date then the imaging device will not operate and a message will be displayed to the operator.

33. The method of claim 22, wherein the method further comprises reading from memory on the imaging device a date the imaging device was last sterilized.

34. The method of claim 33, wherein the control unit reads the date the imaging device was last sterilized from memory and compares that date to a predetermined date and if said date the imaging device was sterilized is beyond the predetermined date the imaging device will not operate and a message will be displayed to the operator.

35. The method of claim 22, wherein the method further comprises storing in memory setting changes made during use of the imaging device.

36. The method of claim 22, wherein the method further comprises recording a duration between a time when the imaging device is turned off and a time when the imaging device is turned back on and recording the duration to memory.

37. The method of claim 36, wherein the method further comprises using the control unit to compare the duration of time recorded in memory to a predetermined duration and if the duration of time recorded in memory is greater than the predetermined duration, the imaging device is prevented from operating and an error message is displayed to an operator.

38. The method of claim 22, wherein the method further comprises reading safety data written to memory on the imaging device using the control unit and comparing the safety data to predetermined values and if said safety data falls outside the predetermined values the imaging device is prevented from operating due to failure to meet safety standards.

39. The method of claim 22, wherein the method further comprises resetting said memory.

40. An imaging system comprising:
a control unit comprising an imaging device input; and
a sterilized single use imaging device comprising:
a housing;
a memory;
an image sensor;
an opening configured to facilitate the transmission of light from optics to the image sensor;
wherein a serial number is stored in said memory for providing identification of the imaging device; and
a communication connection between said imaging device and said control unit.

41. The imaging system of claim 40, wherein said image sensor is electrically connected to a main circuit having the memory thereon.

42. The imaging system of claim 40, wherein the system further comprises a counting circuit that is configured to cause a count value to be recorded in said memory for each time the imaging device is used.

43. The imaging system of claim 40, wherein a timing circuit causes a date and time value to be recorded in said memory when a main circuit is powered on and said timing circuit further records the amount of time the imaging device is in use in said memory.

44. The imaging system of claim 40, wherein the system further comprises data recorded in memory representing a date the imaging device was last sterilized.

45. The imaging system of claim 40, wherein the system further comprises data recorded in memory representing user settings.

46. The imaging system of claim 40, wherein the system further comprises data recorded in memory representing procedure specific settings.

47. The imaging system of claim 40, wherein the system further comprises data recorded in memory representing a location of manufacture.

48. The imaging system of claim 40, wherein the system further comprises data recorded in memory representing a date of manufacture.

49. The imaging system of claim 40, wherein the system further comprises data recorded in memory representing a date the imaging device was last quality control checked.

50. The imaging system of claim 40, wherein the system further comprises imaging device diagnostic data for use with a second complimentary apparatus.

51. The imaging system of claim 40, wherein the control unit comprises video outputs; and wherein the system further comprises an electronic communication circuit that is a tether of wires having an electronic connector configured to mate with a corresponding electronic connector on said control unit.

52. The imaging system of claim 51, wherein said tether of wires comprises a ball configured to mechanically communicate with a corresponding socket structure of said housing.

53. The imaging system of claim 52, wherein an "O" ring seal is disposed about said ball thereby forming a seal between said ball and said corresponding socket.

54. The imaging system of claim 40, wherein the system further comprises an electronic communication circuit that is a wireless communication transceiver configured to communicate wirelessly with a corresponding transceiver on said control unit.

55. The imaging system of claim 40, wherein radio frequency identification is used to provide identifying information.

56. The imaging system of claim 40, wherein said imaging device further comprises a heat sink.

57. The imaging system of claim 41, wherein the system further comprises a counting circuit that is configured to cause a count value to be recorded in said memory for each time the imaging device is used.

58. The imaging system of claim 41, wherein the system further comprises a timing circuit that causes a date and time value to be recorded in said memory when a main circuit is powered on and said timing circuit further records the amount of time the imaging device is in use in said memory.

59. The imaging system of claim 40, wherein the system further comprises LED indications of imaging device status.

60. The imaging system of claim 40, wherein the system further comprises a touch screen LCD panel that is positional by a user in a plurality of positions.

61. A method for renewing a single use imaging device comprising:
writing to a memory on said imaging device a value indicating that the imaging device has been sterilized;
performing a quality control check; and
sterilizing and packaging said single use imaging device.

62. The method claim 61, wherein the method comprises reading a serial number stored in said memory of said imaging device for providing identification of the imaging device.

63. The method of claim 61, wherein the method comprises reading a count value recorded in said memory of said imaging device for each time the imaging device is used.

64. The method of claim 61, wherein the method comprises reading a date and time value recorded in said memory of said imaging device representing the amount of time the imaging device is in use.

65. The method of claim 61, wherein the method comprises reading data representing when the imaging device was most recently sterilized.

66. The method of claim 61, wherein the method comprises reading data representing user settings recorded in said memory of said imaging device.

67. The method of claim 61, wherein the method comprises reading data representing procedure specific settings recorded in said memory of said imaging device.

68. The method of claim 61, wherein the method comprises reading data recorded in memory of said imaging device representing a location of most recent use.

69. The method of claim 61, wherein the method comprises reading data recorded in memory representing a date the imaging device was last quality control checked.

70. The imaging device of claim 16, wherein said wireless communication uses a wireless technology selected from a group comprising: radio frequencies, infrared, ultrasonic, and optical.

71. A system for providing a single use imaging device to a user in a sterilized environment comprising:
a control unit,
a sterilized single use imaging device comprising:
a housing,
an image sensor,
an optic mount in said housing configured for receiving optics,
an opening proximate to said optic mount and configured to facilitate transmission of light from said optics to said image sensor,
a memory comprising data representing characteristics of the imaging device, and
an electronic communication circuit configured for providing electronic communication between said imaging device and a control unit,
a security code for verifying validity of the imaging device,
a data server for providing data regarding the security code to the control unit, wherein said control unit is configured to validate the security code of the imaging device prior to use.

72. The system of claim 71 wherein said data server is configured to communicate with the control unit over a network.

73. The system of claim 71 further comprising a memory device configured for receiving data from said data server and configured for transferring data to said control unit.

74. The system of claim 71 wherein said security code for validating imaging device use comprises data regarding inventory control.

75. The system of claim 71 wherein said security code for validating imaging device use comprises data regarding safety control.

76. The system of claim 71 wherein said security code for validating imaging device use comprises data regarding recall information.

* * * * *